(12) United States Patent
Haisma et al.

(10) Patent No.: US 11,352,626 B2
(45) Date of Patent: *Jun. 7, 2022

(54) OLIGONUCLEOTIDES MATCHING COL7A1 EXON 73 FOR EPIDERMOLYSIS BULLOSA THERAPY

(71) Applicant: WINGS THERAPEUTICS, INC., Berkeley, CA (US)

(72) Inventors: Elisabeth Marlene Haisma, The Hague (NL); Marko Potman, Oegstgeest (NL); Wouter Beumer, Voorburg (NL); Vera Brinks, Leiden (NL)

(73) Assignee: Wings Therapeutics, Inc., Berkeley, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/746,403

(22) Filed: Jan. 17, 2020

(65) Prior Publication Data

US 2020/0399638 A1  Dec. 24, 2020

Related U.S. Application Data

(63) Continuation of application No. 15/554,420, filed as application No. PCT/EP2016/055360 on Mar. 11, 2016, now Pat. No. 10,563,198.

(30) Foreign Application Priority Data

Mar. 11, 2015  (GB) ..................... 1504124

(51) Int. Cl.
  *A61K 48/00* (2006.01)
  *C07H 21/02* (2006.01)
  *C12N 15/113* (2010.01)

(52) U.S. Cl.
  CPC ........ *C12N 15/113* (2013.01); *C12N 2310/11* (2013.01); *C12N 2310/315* (2013.01); *C12N 2310/321* (2013.01); *C12N 2310/346* (2013.01); *C12N 2320/33* (2013.01)

(58) Field of Classification Search
  CPC ............................ C12N 2310/11; C12N 15/113
  See application file for complete search history.

(56) References Cited

U.S. PATENT DOCUMENTS

| | | | |
|---|---|---|---|
| 5,139,941 | A  | 8/1992 | Muzyczka et al. |
| 6,531,546 | B2 | 3/2003 | Oka et al. |
| 7,101,993 | B1 | 9/2006 | Cook et al. |
| 8,524,880 | B2 | 9/2013 | Wilton et al. |
| 8,735,366 | B2 | 5/2014 | Bauer et al. |
| 2004/0092464 | A1 | 5/2004 | Bennett et al. |
| 2004/0096833 | A1 | 5/2004 | Chiang et al. |
| 2006/0025363 | A1 | 2/2006 | Breitenbach et al. |
| 2007/0054869 | A1 | 3/2007 | Bennett et al. |
| 2014/0199245 | A1 | 7/2014 | McNamara, II et al. |
| 2014/0303236 | A1* | 10/2014 | van Rooij ............. A61P 3/04 514/44 A |

FOREIGN PATENT DOCUMENTS

| | | | |
|---|---|---|---|
| WO | WO-97/41208 | 11/1997 | |
| WO | WO-02/24906 | 3/2002 | |
| WO | WO-03/053369 | 7/2003 | |
| WO | WO-2004/083432 | 9/2004 | |
| WO | WO-2004/083446 | 9/2004 | |
| WO | WO-2005/079822 | 9/2005 | |
| WO | WO-2005/086768 | 9/2005 | |
| WO | WO-2006/000057 | 1/2006 | |
| WO | WO-2006/097701 | 9/2006 | |
| WO | WO-2007/069813 | 6/2007 | |
| WO | WO-2007/089584 | 8/2007 | |
| WO | WO-2008/018795 | 2/2008 | |
| WO | WO-2008/106984 | 9/2008 | |
| WO | WO-2010/001247 | 2/2010 | |
| WO | WO-2012/018257 | 2/2012 | |
| WO | WO-2013/053819 | 4/2013 | |
| WO | WO 2013/053819 A1 * | 4/2013 | ........... C12N 15/113 |
| WO | WO-2013/134248 | 9/2013 | |
| WO | WO 2013/173637 A1 | 11/2013 | |
| WO | WO-2015/004133 | 1/2015 | |
| WO | WO-2016/081296 | 5/2016 | |
| WO | WO-2016/196670 | 12/2016 | |
| WO | WO-2016/202779 | 12/2016 | |
| WO | WO-2017/078526 | 5/2017 | |

OTHER PUBLICATIONS

Elbashir et al. (The EMBO Journal, vol. 20, No. 23, pp. 6877-6888, 2001).*
Abe and Kool, "Flow cytometric detection of specific RNAs in native human cells with quenched autoligating FRET probes," PNAS, 103(2), pp. 263-268 (2006).
Almaani et al., "Identical Glycine Substitution Mutations in Type VII Collagen May Underlie Both Dominant and Recessive Forms of Dystrophic Epidermolysis Bullosa", Acta Derm Venereal, 91, pp. 262-266 (2011).
Chen et al., "Restoration of type VII collagen expression and function in dystrophic epidermolysis bullosa," Nat. Genet., 32(4), pp. 670-675 (2002).
Chiorini et al., "Cloning and characterization of adeno-associated virus type 5," J. Virol., 73(2), pp. 1309-1319 (1999).

(Continued)

*Primary Examiner* — Amy H Bowman

(74) *Attorney, Agent, or Firm* — Morse, Barnes-Brown & Pendleton, P.C.; Lisa M. Warren, Esq.; Erin E. Bryan, Esq.

(57) ABSTRACT

Antisense oligonucleotides capable of preventing or reducing exon 73 inclusion into the human COL7A mRNA are characterized in various ways: (a) the oligonucleotide's sequence includes at most two CpG sequences; (b) the oligonucleotide has a length of no more than 24 nucleotides; (c) the oligonucleotide is capable of annealing to the (SRp40/SC35 binding/ESE) element in exon73. These oligonucleotides can usefully be oligoribonucleotides with modified internucleosidic linkages e.g. phosphorothioate linkages.

15 Claims, 8 Drawing Sheets

Specification includes a Sequence Listing.

(56) References Cited

OTHER PUBLICATIONS

Covaciu et al., "A founder synonymous COL7A1 mutation in three Danish families with dominant dystrophic epidermolysis bullosa pruriginosa identifies exonic regulatory sequences required for exon 87 splicing", British Journal of Dermatology, 165, pp. 678-682 (2011).
Dang et al., "Mutation Analysis and Characterization of COL7A1 Mutations in Dystrophic Epidermolysis Bullosa," Experimental Dermatology, 17, pp. 553-568 (2008).
DATABASE Geneseq [Online], "Human organ specific protein related DNA SEQ:60255," retrieved from EBI accession No. GSN:AUN58914, Database accession No. AUN58914 (2011).
DATABASE Geneseq [Online], "Human tumour suppression/reversion-related DNA sequence SeqID1712," retrieved from EBI accession No. GSN:ADI49209, Database accession No. ADI49209 (2004).
DATABASE Geneseq [Online], "Sequence 513357 from Patent EP2213738," retrieved from EBI accession No. EM_PAT:HD636641, Database accession No. HD636641 (2010).
Dom et al., "Clinical application of CpG-, non-CpG-, and antisense oligodeoxynucleotides as immunomodulators," Curr. Opin. Mol. Ther., 10(1), pp. 10-20 (2008).
Egholm et al., "PNA hybridizes to complementary oligonucleotides obeying the Watson-Crick hydrogen-bonding rules," Nature, 365(6446), pp. 566-568 (1993).
Escamez et al., "The First COL7A1 Mutation Survey in a Large Spanish Dystrophic Epidermolysis Bullosa Cohort: c.6527insC Disclosed as an Unusually Recurrent Mutation," British Journal of Dermatology, 163, pp. 155-161 (2010).
Gorman et al., "Stable alteration of pre-mRNA splicing patterns by modified U7 small nuclear RNAs," Proc. Natl. Acad. Sci. USA, 95(9), pp. 4929-4934 (1998).
Goto et al., "Targeted Skipping of a Single Exon Harboring a Premature Termination Codon Mutation: Implications and Potential for Gene Correction Therapy for Selective Dystrophic Epidermolysis Bullosa Patients," Journal of Investigative Dermatology, 126, pp. 2614-2620 (2006).
Govindaraju et al., "Backbone-extended pyrrolidine peptide nucleic acids (bepPNA): design, synthesis and DNA/RNA binding studies," Chem Commun (Camb), 4, pp. 495-497 (2005).
Keswani et al., "Pseudotyped adeno-associated viral vector tropism and transduction efficiencies in murine wound healing," Wound Repair Regen., 20(4), pp. 592-600 (2012).
Kon et al., "Novel COL7A1 Mutations in Dystrophic Forms of Epidermolysis Bullosa," J. Invest. Dermatol., 111(3), pp. 534-537 (1998).
Kurreck, "Antisense technologies, Improvement through novel chemical modifications," Eur. J. Biochem, 270, pp. 1628-1644 (2003).
Macdonald et al., "Characterization of two types of termination signal for bacteriophage T7 RNA polymerase," J. Mol. Biol., 238(2), pp. 145-158 (1994).
Majlessi et al., "Advantages of 2'—O-methyl oligoribonucleotide probes for detecting RNA targets," Nucleic Acids Research, 26(9), pp. 2224-2229 (1998).
Mehta et al., "Intercellular adhesion molecule-1 suppression in skin by topical delivery of anti-sense oligonucleotides," J. Invest. Dermatol., 115(5), pp. 805-812 (2000).
McClorey et al., "Antisense oligonucleotide-induced exon skipping restores dystrophin expression in vitro in a canine model of DMD," Gene Therapy, 13, pp. 1373-1381 (2006).
Mecklenbeck et al., "A microinjected COL7A7-PAC vector restores synthesis of intact procollagen VII in a dystrophic epidermolysis bullosa keratinocyte cell line," Hum. Gene Ther., 13(13), pp. 1655-1662 (2002).
Morita et al., "2'-0,4'—C-ethylene-bridged nucleic acids (ENA) with nuclease-resistance and high affinity for RNA," Nucleic Acids Res., Suppl. 1, pp. 241-242 (2001).
Nielsen et al., "Sequence-selective recognition of DNA by strand displacement with a thymine-substituted polyamide," Science, 254(5037), pp. 1497-1500 (1991).
Pendaries et al., "Immune reactivity to type VII collagen: implications for gene therapy of recessive dystrophic epidermolysis bullosa," Gene Therapy, 17, pp. 930-937 (2010).
SFTCG 2009 Oral Presentations, Human Gene Therapy, 20, pp. 665-670 (2009).
Shinnick et al., "Hybridization of labeled RNA to DNA in agarose gels," Nucleic Acids Research, 2(10), pp. 1911-1929 (1975).
Spitali et al., "Exon Skipping-Mediated Dystrophin Reading Frame Restoration for Small Mutations", Human Mutation, 30(11), pp. 1527-1534 (2009).
Suter et al., "Double-target antisense U7 snRNAs promote efficient skipping of an aberrant exon in three human β-thalassemic mutations," Hum. Mol. Genet., 8(13), pp. 2415-2423 (1999).
Suzuki et al., "A new PCR-based approach for the preparation of RNA probe," J. Biochem. Biophys. Methods, 62, pp. 251-258 (2005).
Titeux et al. "Gene Therapy for Recessive Dystrophic Epidermolysis Bullosa", Dermatol. Clin., 28(2), pp. 361-366 (2010).
Titeux et al., "SIN retroviral vectors expressing COL7A1 under human promoters for ex vivo gene therapy of recessive dystrophic epidermolysis bullosa," Mol. Ther., 18(8), pp. 1509-1518 (2010).
Turczynski et al., "Antisense-Mediated Exon Skipping to Reframe Transcripts", Exon Skipping: Methods and Protocols; Methods in Molecular Biology, 867, pp. 221-238 (2012).
Van der Akker et al., "Dystrophic epidermolysis bullosa Chapter 6: The genotype-phenotype correlation in dominant dystrophic epidermolysis bullosa," pp. 162-181 (2013).
Varki et al., "Epidermolysis Bullosa II Type VII Collagen Mutations and Phenotype-Genotype Correlations in the Dystrophic Subtypes," J. Med. Genet., 44, pp. 181-192 (2006).
Wraight et al., "Antisense oligonucleotides in cutaneous therapy," Pharmacol. Ther., 90(1), pp. 89-104 (2001).
Wilton et al., "Antisense Oligonucleotide-induced Exon Skipping Across the Human Dystrophin Gene Transcript," Molecular Therapy, 15(7), pp. 1288-1296 (2007).
Aartsma-Rus, Annemieke, et al. "Exonic sequences provide better targets for antisense oiigonucleotides than spiice site sequences in the modulation of Duchenne muscular dystrophy splicing." *Oligonucleotides* 20.2 (2010): 69-77.
Lebedeva, I. V., and C. A. Stein. "Phosphorothioate oligodeoxynucleotides as inhibitors of gene expression: antisense and non-antisense effects." *Applications of antisense therapies to restenosis.* Springer, Boston, MA, 1999. 99-118.

\* cited by examiner

Human exon 73 (201b)

5″ ....agcattctctcttccactcctgcagGGCCCCATCGGCTTTCCTGAGAACGCGGGCTGAAGGGCGACCGTGG
AGACCCTGGCCTCAGGGGCCACCTGGTCTGGCCCTTGGGAGAGGGCCCCCGGGCCTTCCGGCC
TTGCCGGGGAGCCTGGAAAGCCTGGTATTCCCGGGCTCCCAGGCAGGGCTGGGGGTGTGGGAGAGGC
AGGAAGGCCAGGAGAGAGGGgtgaggctgaggctggggggctggccaggaga....3″

FIG. 1

SEQUENCE LISTING

<160> NUMBER OF SEQ ID NOS: 54

<210> SEQ ID NO 1
<211> LENGTH: 201
<212> TYPE: DNA
<213> ORGANISM: Homo sapiens

<400> SEQUENCE: 1
ggccccatcg gctttcctgg agaacgcggg ctgaagggcg accgtggaga ccctggccct      60
caggggccac ctggtctggc ccttggggag aggggccccc ccgggccttc cggccttgcc     120
ggggagcctg gaaagcctgg tattcccggg ctcccaggca gggctggggg tgtgggagag     180
gcaggaaggc caggagagag g                                               201

<210> SEQ ID NO 2
<211> LENGTH: 25
<212> TYPE: DNA
<213> ORGANISM: Homo sapiens

<400> SEQUENCE: 2
agcattctct cttccactcc tgcag                                            25

<210> SEQ ID NO 3
<211> LENGTH: 25
<212> TYPE: DNA
<213> ORGANISM: Homo sapiens

<400> SEQUENCE: 3
gtgaggctgg gggctggcca ggaga                                            25

<210> SEQ ID NO 4
<211> LENGTH: 8
<212> TYPE: RNA

<213> ORGANISM: Homo sapiens

<400> SEQUENCE: 4 uuuccugg                                                                    8

<210> SEQ ID NO 5
<211> LENGTH: 24
<212> TYPE: RNA
<213> ORGANISM: Artificial Sequence
<220> FEATURE:
<223> OTHER INFORMATION: Antisense oligonucleotide

<400> SEQUENCE: 5
ucuccaggaa agccgauggg gccc                                                 24

<210> SEQ ID NO 6
<211> LENGTH: 25
<212> TYPE: RNA
<213> ORGANISM: Artificial Sequence
<220> FEATURE:
<223> OTHER INFORMATION: Antisense oligonucleotide

<400> SEQUENCE: 6
agcccgcguu cuccaggaaa gccga                                                25

<210> SEQ ID NO 7
<211> LENGTH: 25
<212> TYPE: RNA
<213> ORGANISM: Artificial Sequence
<220> FEATURE:
<223> OTHER INFORMATION: Antisense oligonucleotide

<400> SEQUENCE: 7
gucgcccuuc agcccgcguu cucca                                                25

<210> SEQ ID NO 8
<211> LENGTH: 23
<212> TYPE: RNA
<213> ORGANISM: Artificial Sequence
<220> FEATURE:
<223> OTHER INFORMATION: Antisense oligonucleotide

<400> SEQUENCE: 8
acggucgccc uucagcccgc guu                                                  23

<210> SEQ ID NO 9
<211> LENGTH: 25
<212> TYPE: RNA
<213> ORGANISM: Artificial Sequence
<220> FEATURE:
<223> OTHER INFORMATION: Antisense oligonucleotide

<400> SEQUENCE: 9
ccccugaggg ccaggucuc cacgg                                                 25

<210> SEQ ID NO 10
<211> LENGTH: 25
<212> TYPE: RNA
<213> ORGANISM: Artificial Sequence
<220> FEATURE:
<223> OTHER INFORMATION: Antisense oligonucleotide

<400> SEQUENCE: 10
cagaccaggu ggcccugag ggcca                                                 25

```
<210> SEQ ID NO 11
<211> LENGTH: 24
<212> TYPE: RNA
<213> ORGANISM: Artificial Sequence
<220> FEATURE:
<223> OTHER INFORMATION: Antisense oligonucleotide

<400> SEQUENCE: 11
ccaagggcca gaccaggugg cccc                                              24

<210> SEQ ID NO 12
<211> LENGTH: 25
<212> TYPE: RNA
<213> ORGANISM: Artificial Sequence
<220> FEATURE:
<223> OTHER INFORMATION: Antisense oligonucleotide

<400> SEQUENCE: 12
ccagaccagg uggccccuga gggcc                                             25

<210> SEQ ID NO 13
<211> LENGTH: 22
<212> TYPE: RNA
<213> ORGANISM: Artificial Sequence
<220> FEATURE:
<223> OTHER INFORMATION: Antisense oligonucleotide

<400> SEQUENCE: 13
ucuccccaag ggccagacca gg                                                22

<210> SEQ ID NO 14
<211> LENGTH: 24
<212> TYPE: RNA
<213> ORGANISM: Artificial Sequence
<220> FEATURE:
<223> OTHER INFORMATION: Antisense oligonucleotide

<400> SEQUENCE: 14
ggaaggcccg ggggggcccc ucuc                                              24

<210> SEQ ID NO 15
<211> LENGTH: 24
<212> TYPE: DNA
<213> ORGANISM: Artificial Sequence
<220> FEATURE:
<223> OTHER INFORMATION: Antisense oligonucleotide

<400> SEQUENCE: 15
ccggcaaggc cggaaggccc gggg                                              24

<210> SEQ ID NO 16
<211> LENGTH: 24
<212> TYPE: RNA
<213> ORGANISM: Artificial Sequence
<220> FEATURE:
<223> OTHER INFORMATION: Antisense oligonucleotide

<400> SEQUENCE: 16
aggcuuucca ggcuccccgg caag                                              24

<210> SEQ ID NO 17
<211> LENGTH: 24
<212> TYPE: RNA
<213> ORGANISM: Artificial Sequence
<220> FEATURE:
<223> OTHER INFORMATION: Antisense oligonucleotide
```

```
<400> SEQUENCE: 17
cgggaauacc aggcuuucca ggcu                                              24

<210> SEQ ID NO 18
<211> LENGTH: 23
<212> TYPE: RNA
<213> ORGANISM: Artificial Sequence
<220> FEATURE:
<223> OTHER INFORMATION: Antisense oligonucleotide

<400> SEQUENCE: 18
ugccugggag cccgggaaua cca                                               23

<210> SEQ ID NO 19
<211> LENGTH: 24
<212> TYPE: RNA
<213> ORGANISM: Artificial Sequence
<220> FEATURE:
<223> OTHER INFORMATION: Antisense oligonucleotide

<400> SEQUENCE: 19
cccacacccc cagcccugcc uggg                                              24

<210> SEQ ID NO 20
<211> LENGTH: 22
<212> TYPE: RNA
<213> ORGANISM: Artificial Sequence
<220> FEATURE:
<223> OTHER INFORMATION: Antisense oligonucleotide

<400> SEQUENCE: 20
ccucucccac accccagcc cu                                                 22

<210> SEQ ID NO 21
<211> LENGTH: 23
<212> TYPE: RNA
<213> ORGANISM: Artificial Sequence
<220> FEATURE:
<223> OTHER INFORMATION: Antisense oligonucleotide

<400> SEQUENCE: 21
ucucuccugg ccuuccugcc ucu                                               23

<210> SEQ ID NO 22
<211> LENGTH: 22
<212> TYPE: RNA
<213> ORGANISM: Artificial Sequence
<220> FEATURE:
<223> OTHER INFORMATION: Antisense oligonucleotide

<400> SEQUENCE: 22
cacccucucu ccuggccuuc cu                                                22

<210> SEQ ID NO 23
<211> LENGTH: 22
<212> TYPE: RNA
<213> ORGANISM: Artificial Sequence
<220> FEATURE:
<223> OTHER INFORMATION: Antisense oligonucleotide

<400> SEQUENCE: 23
ccagccucac ccucucuccu gg                                                22

<210> SEQ ID NO 24
<211> LENGTH: 23
```

```
<212> TYPE: RNA
<213> ORGANISM: Artificial Sequence
<220> FEATURE:
<223> OTHER INFORMATION: Antisense oligonucleotide

<400> SEQUENCE: 24
cuccaggaaa gccgaugggg ccc                                          23

<210> SEQ ID NO 25
<211> LENGTH: 22
<212> TYPE: RNA
<213> ORGANISM: Artificial Sequence
<220> FEATURE:
<223> OTHER INFORMATION: Antisense oligonucleotide

<400> SEQUENCE: 25
uccaggaaag ccgauggggc cc                                           22

<210> SEQ ID NO 26
<211> LENGTH: 21
<212> TYPE: RNA
<213> ORGANISM: Artificial Sequence
<220> FEATURE:
<223> OTHER INFORMATION: Antisense oligonucleotide

<400> SEQUENCE: 26
ccaggaaagc cgauggggcc c                                            21

<210> SEQ ID NO 27
<211> LENGTH: 24
<212> TYPE: RNA
<213> ORGANISM: Artificial Sequence
<220> FEATURE:
<223> OTHER INFORMATION: Antisense oligonucleotide

<400> SEQUENCE: 27
cuccaggaaa uccgaugggg cccu                                         24

<210> SEQ ID NO 28
<211> LENGTH: 24
<212> TYPE: RNA
<213> ORGANISM: Artificial Sequence
<220> FEATURE:
<223> OTHER INFORMATION: Antisense oligonucleotide

<400> SEQUENCE: 28
uccaggaaag ccgauggggc ccug                                         24

<210> SEQ ID NO 29
<211> LENGTH: 24
<212> TYPE: RNA
<213> ORGANISM: Artificial Sequence
<220> FEATURE:
<223> OTHER INFORMATION: Antisense oligonucleotide

<400> SEQUENCE: 29
ccaggaaagc cgauggggcc cugc                                         24

<210> SEQ ID NO 30
<211> LENGTH: 24
<212> TYPE: RNA
<213> ORGANISM: Artificial Sequence
<220> FEATURE:
<223> OTHER INFORMATION: Antisense oligonucleotide

<400> SEQUENCE: 30
```
aggaaagccg augggggcccu gcag                                              24

<210> SEQ ID NO 31
<211> LENGTH: 24
<212> TYPE: RNA
<213> ORGANISM: Artificial Sequence
<220> FEATURE:
<223> OTHER INFORMATION: Antisense oligonucleotide

<400> SEQUENCE: 31
gaaagccgau ggggcccugc agga                                               24

<210> SEQ ID NO 32
<211> LENGTH: 24
<212> TYPE: RNA
<213> ORGANISM: Artificial Sequence
<220> FEATURE:
<223> OTHER INFORMATION: Antisense oligonucleotide

<400> SEQUENCE: 32
aagccgaugg ggcccugcag gagu                                               24

<210> SEQ ID NO 33
<211> LENGTH: 24
<212> TYPE: RNA
<213> ORGANISM: Artificial Sequence
<220> FEATURE:
<223> OTHER INFORMATION: Antisense oligonucleotide

<400> SEQUENCE: 33
gccgaugggg cccugcagga gugg                                               24

<210> SEQ ID NO 34
<211> LENGTH: 23
<212> TYPE: RNA
<213> ORGANISM: Artificial Sequence
<220> FEATURE:
<223> OTHER INFORMATION: Antisense oligonucleotide

<400> SEQUENCE: 34 gaugggggccc ugcaggagug gaa                                               23

<210> SEQ ID NO 35
<211> LENGTH: 21
<212> TYPE: RNA
<213> ORGANISM: Artificial Sequence
<220> FEATURE:
<223> OTHER INFORMATION: Antisense oligonucleotide

<400> SEQUENCE: 35
cguucuccag gaaagccgau g                                                  21

<210> SEQ ID NO 36
<211> LENGTH: 22
<212> TYPE: RNA
<213> ORGANISM: Artificial Sequence
<220> FEATURE:
<223> OTHER INFORMATION: Antisense oligonucleotide

<400> SEQUENCE: 36
ccugagggcc agggucucca cg                                                 22

<210> SEQ ID NO 37
<211> LENGTH: 30
<212> TYPE: RNA
<213> ORGANISM: Artificial Sequence

```
<220> FEATURE:
<223> OTHER INFORMATION: Antisense oligonucleotide

<400> SEQUENCE: 37
ucuccacggu cgcccuucag cccgcguucu                                          30

<210> SEQ ID NO 38
<211> LENGTH: 25
<212> TYPE: RNA
<213> ORGANISM: Artificial Sequence
<220> FEATURE:
<223> OTHER INFORMATION: Antisense oligonucleotide

<400> SEQUENCE: 38
ucuccacggu cgcccuucag cccgc                                               25

<210> SEQ ID NO 39
<211> LENGTH: 18
<212> TYPE: RNA
<213> ORGANISM: Artificial Sequence
<220> FEATURE:
<223> OTHER INFORMATION: Antisense oligonucleotide

<400> SEQUENCE: 39
uccaggaaag ccgauggg                                                       18

<210> SEQ ID NO 40
<211> LENGTH: 17
<212> TYPE: RNA
<213> ORGANISM: Artificial Sequence
<220> FEATURE:
<223> OTHER INFORMATION: Antisense oligonucleotide

<400> SEQUENCE: 40
uccaggaaag ccgaugg                                                        17

<210> SEQ ID NO 41
<211> LENGTH: 16
<212> TYPE: RNA
<213> ORGANISM: Artificial Sequence
<220> FEATURE:
<223> OTHER INFORMATION: Antisense oligonucleotide

<400> SEQUENCE: 41
uccaggaaag ccgaug                                                         16

<210> SEQ ID NO 42
<211> LENGTH: 18
<212> TYPE: RNA
<213> ORGANISM: Artificial Sequence
<220> FEATURE:
<223> OTHER INFORMATION: Antisense oligonucleotide

<400> SEQUENCE: 42
cuccaggaaa gccgaugg                                                       18

<210> SEQ ID NO 43
<211> LENGTH: 18
<212> TYPE: RNA
<213> ORGANISM: Artificial Sequence
<220> FEATURE:
<223> OTHER INFORMATION: Antisense oligonucleotide

<400> SEQUENCE: 43
ucuccaggaa agccgaug                                                       18
```

```
<210> SEQ ID NO 44
<211> LENGTH: 10
<212> TYPE: RNA
<213> ORGANISM: Artificial Sequence
<220> FEATURE:
<223> OTHER INFORMATION: Antisense oligonucleotide

<400> SEQUENCE: 44
uccaggaaag                                                          10

<210> SEQ ID NO 45
<211> LENGTH: 18
<212> TYPE: RNA
<213> ORGANISM: Artificial Sequence
<220> FEATURE:
<223> OTHER INFORMATION: Antisense oligonucleotide

<400> SEQUENCE: 45
cccaucggcu uuccugga                                                 18

<210> SEQ ID NO 46
<211> LENGTH: 17
<212> TYPE: RNA
<213> ORGANISM: Artificial Sequence
<220> FEATURE:
<223> OTHER INFORMATION: RNA binding sequence

<400> SEQUENCE: 46
ccaucggcuu uccugga                                                  17

<210> SEQ ID NO 47
<211> LENGTH: 16
<212> TYPE: RNA
<213> ORGANISM: Artificial Sequence
<220> FEATURE:
<223> OTHER INFORMATION: RNA binding sequence

<400> SEQUENCE: 47
caucggcuuu ccugga                                                   16

<210> SEQ ID NO 48
<211> LENGTH: 18
<212> TYPE: RNA
<213> ORGANISM: Artificial Sequence
<220> FEATURE:
<223> OTHER INFORMATION: RNA binding sequence

<400> SEQUENCE: 48
ccaucggcuu uccuggag                                                 18

<210> SEQ ID NO 49
<211> LENGTH: 18
<212> TYPE: DNA
<213> ORGANISM: Artificial Sequence
<220> FEATURE:
<223> OTHER INFORMATION: RNA binding sequence

<400> SEQUENCE: 49
caucggcuuu ccuggaga                                                 18

<210> SEQ ID NO 50
<211> LENGTH: 10
<212> TYPE: RNA
<213> ORGANISM: Artificial Sequence
<220> FEATURE:
<223> OTHER INFORMATION: RNA binding sequence
```

```
<400> SEQUENCE: 50
cuuuccugga                                                              10

<210> SEQ ID NO 51
<211> LENGTH: 18
<212> TYPE: DNA
<213> ORGANISM: Artificial Sequence
<220> FEATURE:
<223> OTHER INFORMATION: Primer

<400> SEQUENCE: 51
gctggcatca aggcatct                                                     18

<210> SEQ ID NO 52
<211> LENGTH: 20
<212> TYPE: DNA
<213> ORGANISM: Artificial Sequence
<220> FEATURE:
<223> OTHER INFORMATION: Primer

<400> SEQUENCE: 52
tcctttctct ccccgttctc                                                   20

<210> SEQ ID NO 53
<211> LENGTH: 251
<212> TYPE: DNA
<213> ORGANISM: Homo sapiens

<400> SEQUENCE: 53
agcattctct cttccactcc tgcagggccc catcggcttt cctggagaac gcgggctgaa        60
gggcgaccgt ggagaccctg gccctcaggg gccacctggt ctggcccttg gggagagggg       120
ccccccgggg ccttccggcc ttgccgggga gcctggaaag cctggtattc ccgggctccc       180
aggcagggct gggggtgtgg gagaggcagg aaggccagga gagagggtga ggctgggggc       240
tggccaggag a                                                           251

<210> SEQ ID NO 54
<211> LENGTH: 100
<212> TYPE: DNA
<213> ORGANISM: Artificial Sequence
<220> FEATURE:
<223> OTHER INFORMATION: Antisense oligonucleotide

<400> SEQUENCE: 54
agcauucucu cuuccacucc ugcagggccc caucggcuuu ccuggagaac gcgggcugaa        60
gggcgaccgu ggagacccug gcccucaggg gccaccuggu                             100
```

OLIGONUCLEOTIDES MATCHING COL7A1 EXON 73 FOR EPIDERMOLYSIS BULLOSA THERAPY

CROSS-REFERENCE TO RELATED APPLICATIONS

This application is a continuation of U.S. patent application Ser. No. 15/554,420, filed on Aug. 29, 2017 which is a § 371 national phase of International Application No. PCT/EP2016/055360, filed on Mar. 11, 2016, which claims the benefit of United Kingdom patent application 1504124.7, filed Mar. 11, 2015, the complete contents of which are hereby incorporated herein by reference for all purposes.

SEQUENCE LISTING

The instant application contains a Sequence Listing which has been submitted in ASCII format via EFS-Web and is hereby incorporated by reference in its entirety. The ASCII copy, created on Dec. 4, 2017, is named PQR-006_SL.txt and is 15,185 bytes in size.

FIELD OF THE INVENTION

The present invention is concerned with oligonucleotides suitable for use in treating human disease. More in particular the present invention is concerned with antisense oligonucleotides suitable for the treatment of dystrophic epidermolysis bullosa.

DISEASE BACKGROUND

Epidermolysis Bullosa (EB) is a group of heritable skin diseases, which are characterized by chronic fragility and blistering of the skin and mucous membranes. Depending on the subtype, the spectrum of symptoms of the EB is very broad, ranging from minimal skin fragility to very severe symptoms with general complications. Worldwide about 350,000 patients are affected. In some forms of EB, also nails, hair and teeth may be involved. The main types of EB include EB Simplex (EBS), Junctional EB (JEB), Dystrophic EB (DEB) and Kindler syndrome (KS).

DEB affects about 25% of EB patients, can be either dominantly or recessively inherited, and involves defects in Type VII collagen (COL7A1, omim 120120). COL7A1 encoding the alpha-1 chain of collagen VII. Collagen VII functions as an anchoring fibril of the upper part of the dermis to the lamina densa (part of the basement membrane). Following post-translational modification three identical alpha-1 chains fold together with their collagenous triple helix domain. Subsequently, antiparallel dimers are formed that align to form the anchoring fibrils. Collagen VII is synthesized in the skin by keratinocytes and dermal fibroblasts. DEB disease severity roughly correlates with the amount of type VII collagen expression at the basement membrane zone.

Characteristics of Dominant Dystrophic EB (DDEB) include blistering that may be localized to the hands, feet, elbows and knees or generalized. Common findings include scarring, milia, mucous membrane involvement, and abnormal or absent nails. Recessive Dystrophic EB (RDEB) is typically more generalized and severe than DDEB. In addition to the findings of DDEB, other common manifestations of RDEB include malnutrition, anemia, osteoporosis, esophageal strictures, growth retardation, webbing, or fusion of the fingers and toes causing mitten deformity (pseudo-syndactyly), development of muscle contractures, malformation of teeth, microstomia and scarring of the eye. The risk of squamous cell carcinoma is greatly increased in this group as well as death from metastatic squamous cell carcinoma.

Within the gene COL7A1 more than 400 different mutations are known. One of the most prevalent affected exons (18% of patients) is exon 73 with about 40 known mutations, most often missense mutations or mutations leading to premature termination codons (PTCs) and glycine substitutions. Currently there is no treatment for DEB, only palliative care is performed. Severe forms of RDEB impose a high cost on society's healthcare budget: the average costs of dressings and medication is about €200,000 per patient per year.

WO2013/053819 of Institut National de la Sante et de la Recherche Médicale (INSERM) discloses two antisense oligonucleotides targeting exon 73, causing the entire exon to be skipped from the mRNA. The exon-73-deficient mRNA is translated into a functional polypeptide that, although being shorter than the wt protein, behaves very similar to wild-type collagen VIIa. One oligonucleotide disclosed is 25 nucleotides in length, displaying a skipping efficiency of 69%, while the other is 30 nucleotides in length, displaying 93% skipping efficiency.

SUMMARY OF THE INVENTION

Although the longer exon-skipping AON in WO2013/053819 appears to display satisfactory exon skipping efficiency, its length and some other characteristics make it less preferred from the perspective of developing such a molecule for human therapeutic use. Besides, it appears that this oligonucleotide produces intermediate bands that are neither representative of wild-type, nor of exon 73-free mRNAs. Although it is not known whether these bands have clinical relevance, producing by-products is less preferred from a regulatory and safety standpoint. Hence, there remains a need for further and improved therapies to treat DEB.

Thus the invention provides an antisense oligonucleotide capable of preventing or reducing exon 73 inclusion into the human COL7A1 mRNA, when said mRNA is produced by splicing from a pre-mRNA in a mammalian cell; characterized in that (a) the oligonucleotide's sequence includes at most two CpG sequences and/or (b) the oligonucleotide has a length of no more than 24 nucleotides. Advantageously, the oligonucleotide has both properties (a) and (b).

The invention also provides an antisense oligonucleotide capable of preventing or reducing exon 73 inclusion into the human COL7A1 mRNA, when said mRNA is produced by splicing from a pre-mRNA in a mammalian cell, characterized in that the oligonucleotide is capable of annealing to the (SRp40/SC35 binding/ESE) element in exon 73 characterized by the sequence 5'-UUUCCUGG-3' (SEQ ID NO: 4). This oligonucleotide can have properties (a) and/or (b) as discussed above.

Oligonucleotides of the invention can usefully be oligoribonucleotides with modified internucleosidic linkages e.g. phosphorothioate linkages. They can also have modified sugars e.g. with 2'-O-methyl substituted sugar moieties. These and other details of the oligonucleotides are discussed below.

DESCRIPTION OF THE FIGURES

FIG. 1 shows a nucleotide sequence (SEQ ID NO: 53) which includes the human Col7A1 exon 73 (SEQ ID NO: 1;

upper case) with its 5' and 3' flanking intron boundaries (SEQ ID NOs: 2 & 3; lower case)

Figure 2:
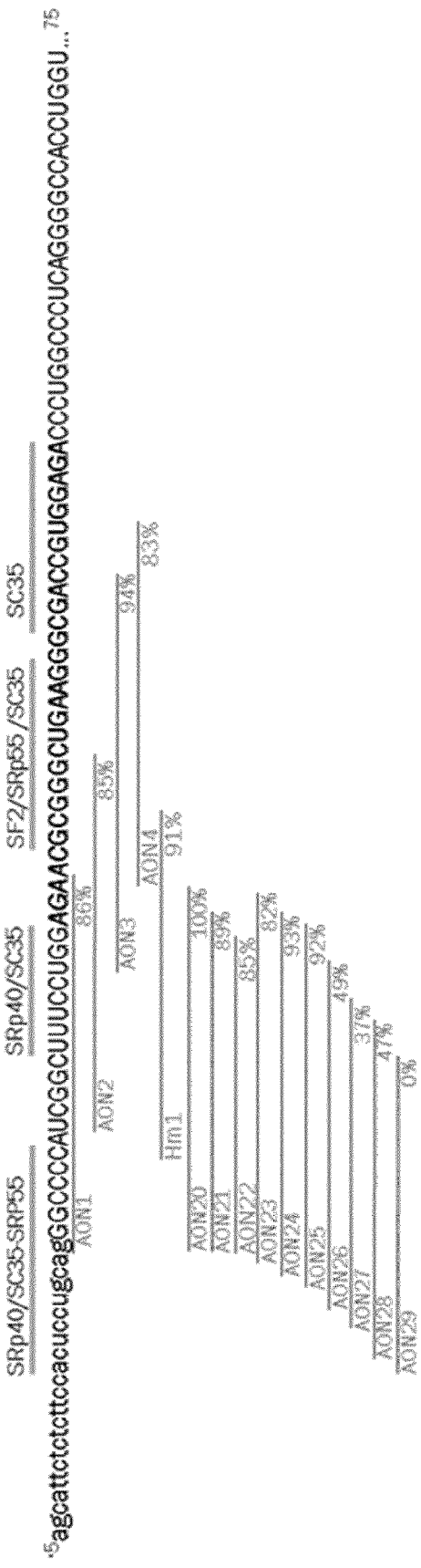

FIG. 2 shows a nucleotide sequence (SEQ ID NO: 54) which includes the location of SR protein binding sites in exon 73 and the location of AONs.

Figure 3:
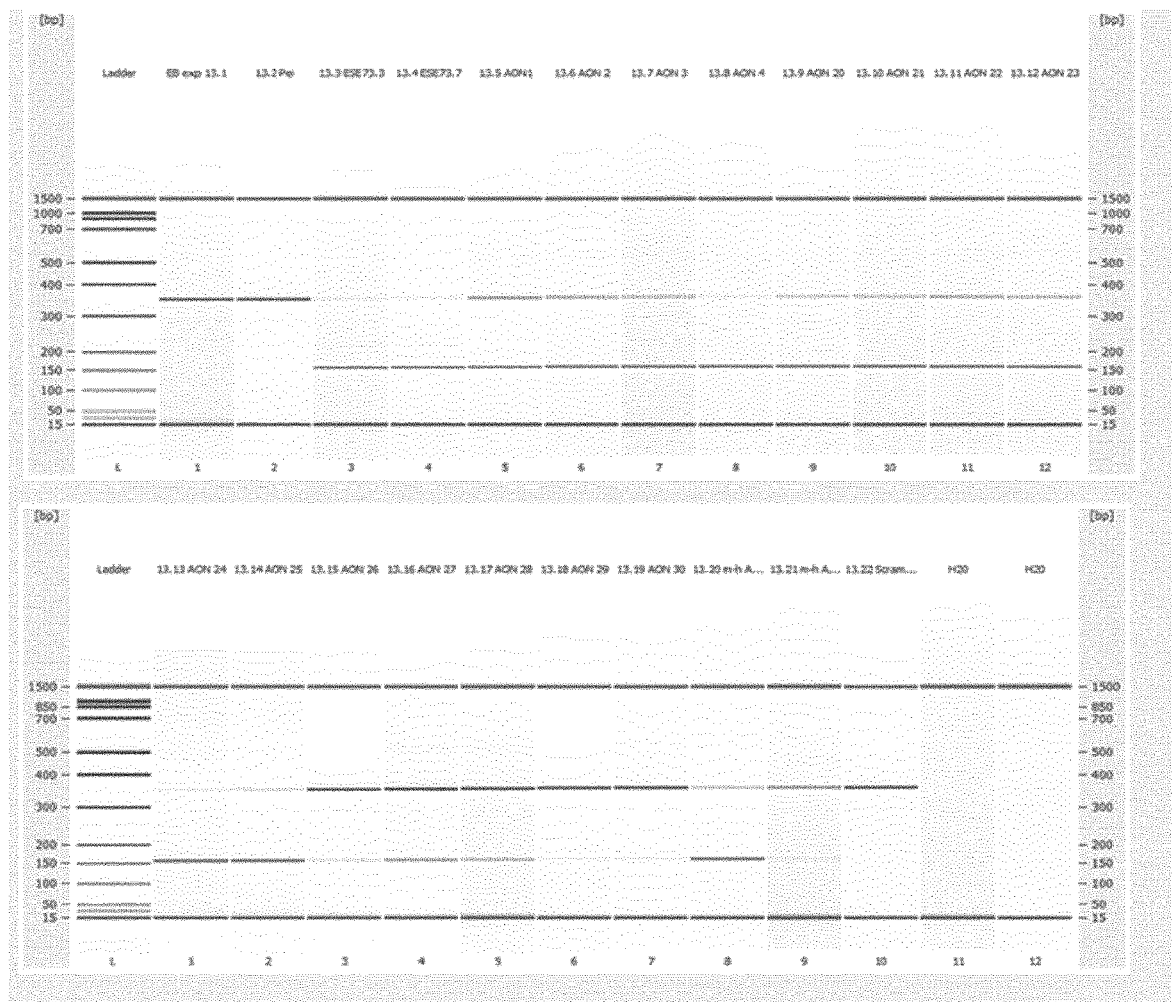

FIG. 3 shows lab-on-a-chip results for exon skipping on primary human fibroblasts (HPF) cells. The full-length mRNA gives a band at ~350 bp, whereas mRNA with excluded exon 73 is ~150 bp.

Figure 4:
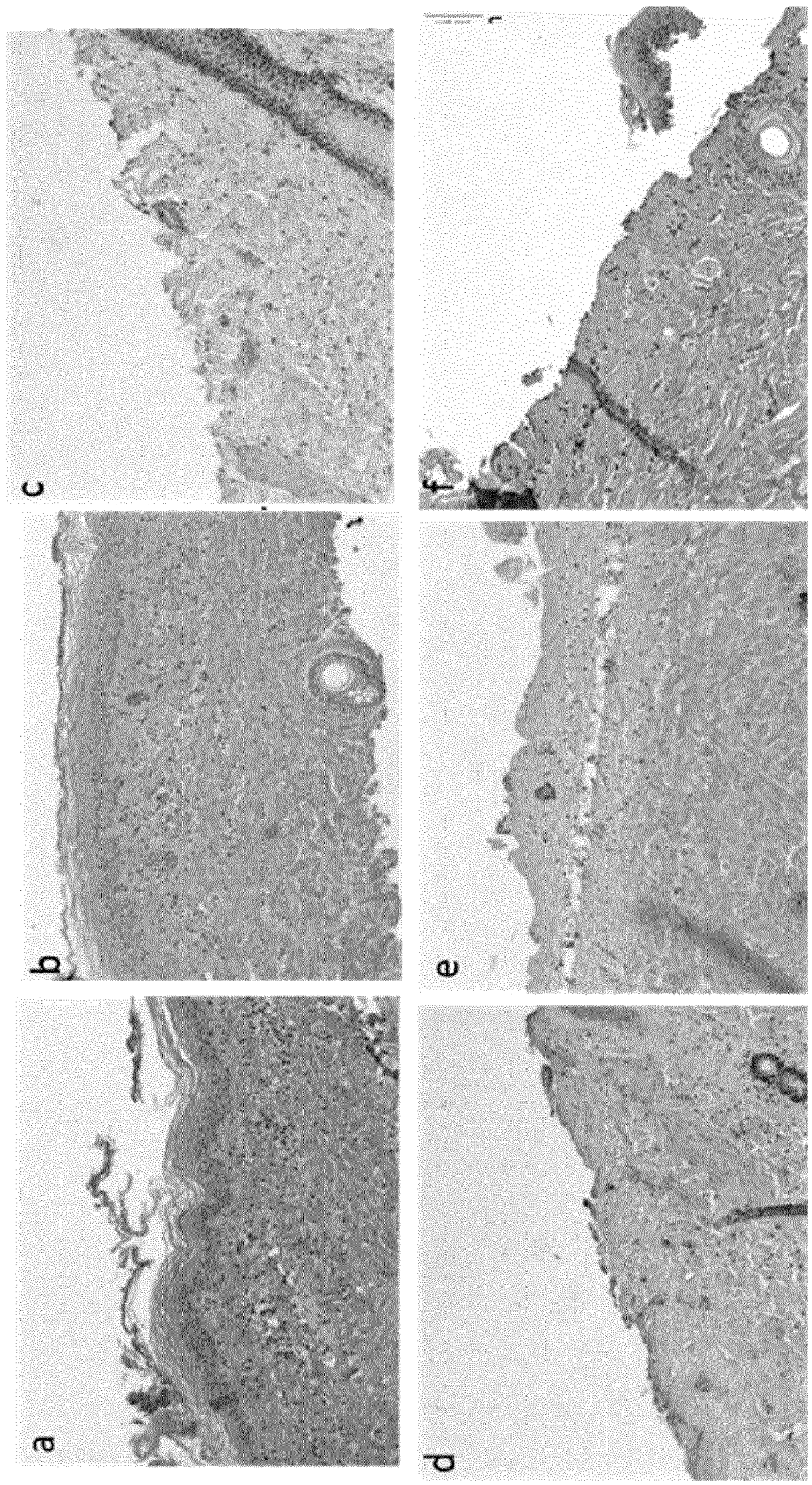

FIG. 4 shows the histological results of delivery of mh-AON1 formulated in PBS using an ex vivo porcine skin model. A-B shows the results of having 25 µg of mh-AON on intact skin for 24 hours, C—F shows the results of having 25 µg of mh-AON1 on blister-like skin, with the complete epidermis removed. C-D: incubation for 24 hours. E-F: incubation for 48 hours. mh-AON1 is stained (red). Scale bar is 100 µm.

Figure 5:
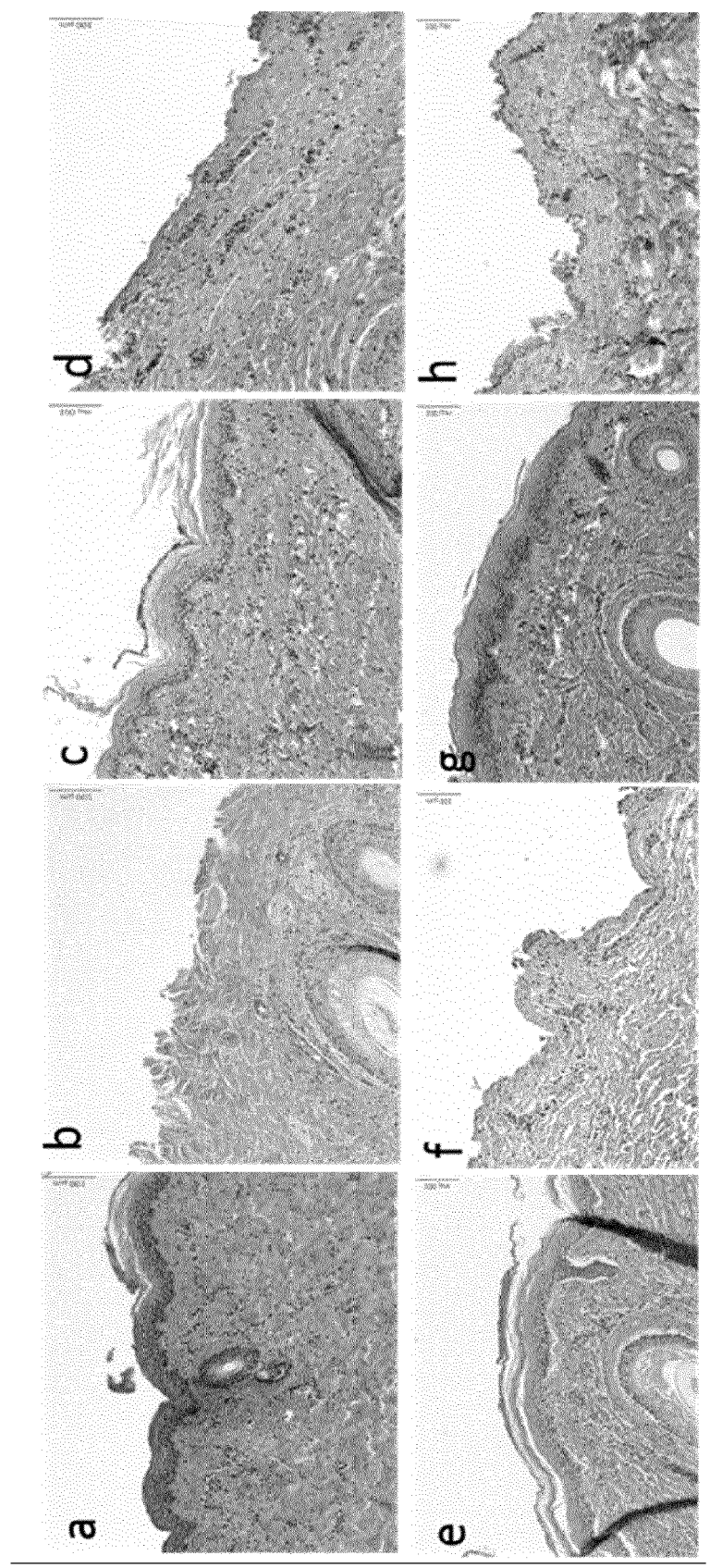

FIG. 5 shows the histological results of delivery of mh-AON1 formulated into three different hydrogels using the same ex vivo porcine skin model as for FIG. 4. A-B shows the results of porcine skin treated with saline controls (A) with intact epidermis and (B) with removed epidermis. C-D shows the porcine skin treated with 50 µg mh-AON1-cy5 mixed in Flaminal®, (C) with intact epidermis (D) with epidermis removed. E-F shows the results with porcine skin treated with 50 µg mh-AON1-cy5 mixed in carbomer hydrogel (E) with intact epidermis and (F) with epidermis removed. G-H shows the results with porcine skin treated with 50 µg mh-AON1-cy5 mixed in hypromellose hydrogel (G) intact skin and (H) with removed epidermis. Scale bar indicates 100 µm. mh-AON1 is stained (red).

Figure 6:
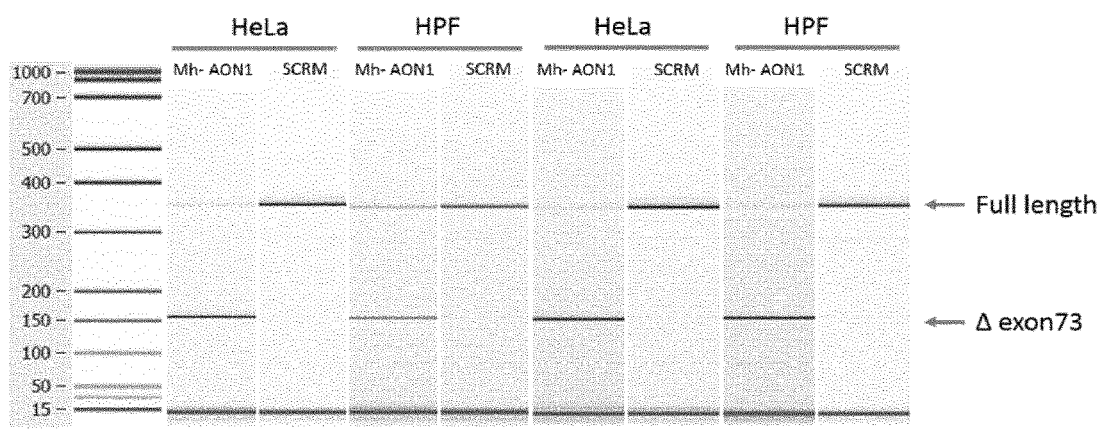

FIG. 6 shows lab-on-a-chip results of splicing products of COL7A1 mRNA after treatment with mh-AON1 or the scrambled variant (SCRM) as a control oligo. Two different cell types we tested (HeLa and HPF), both with 100 nM oligonucleotide for either 24 h or 40 h. Different COL7A1 mRNA products are formed after treatment with mh-AON1 or control oligo (including and excluding exon 73). The different mRNA products were analysed for length; 350 fragment represents the wild type, full length, mRNA and the 150 nucleotide fragment the modulated mRNA product.

Figure 7:
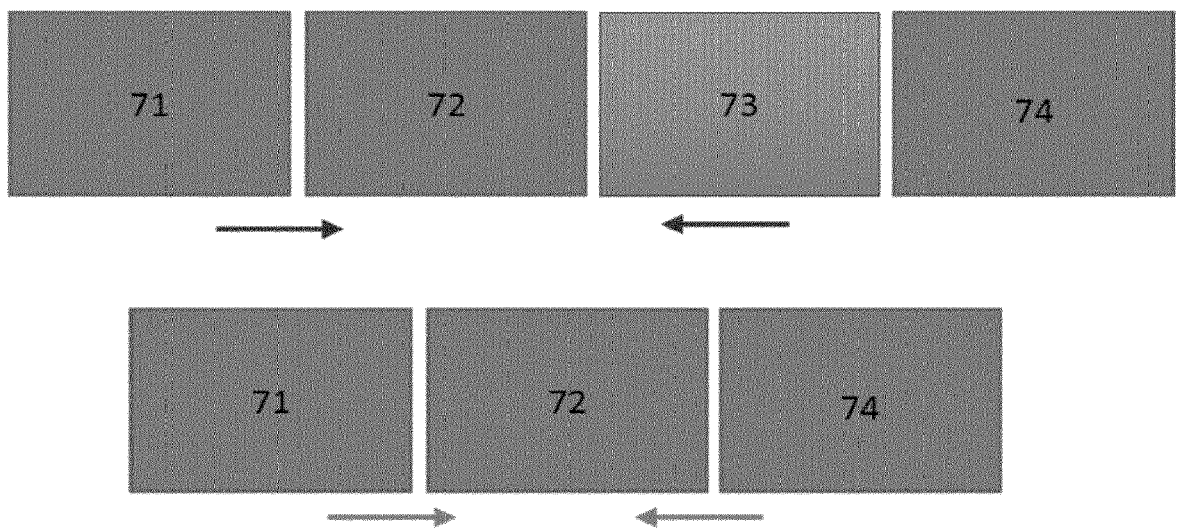

FIG. 7 shows primer design for the ddPCR assay, two different primer combinations were designed to PCR either only the wild type product or the Δ exon 73 product. Upper row: primer pair for the wild type; Lower row: primer pair for the skipped exon 73.

Figure 8A:
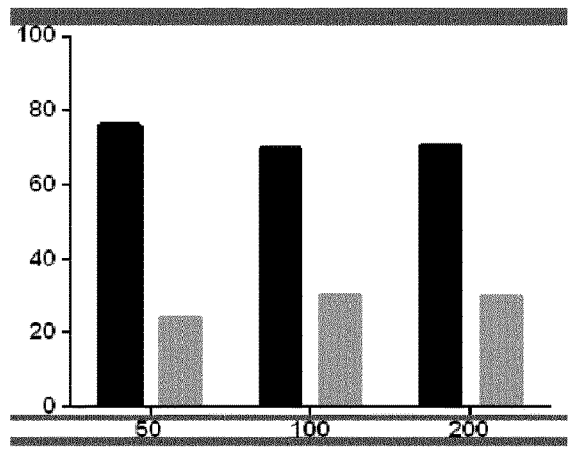
Figure 8B:
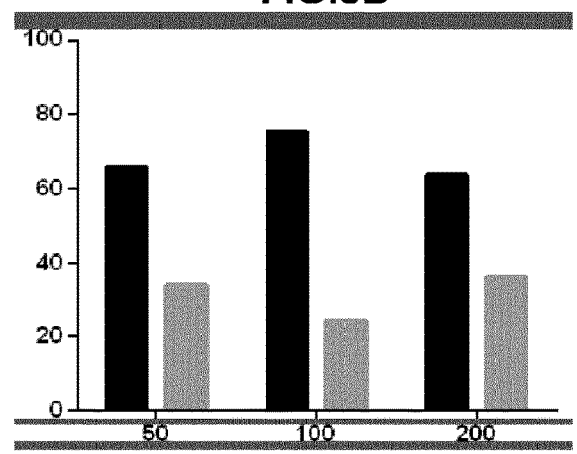

FIGS. 8A-B show the absolute quantification of COL7A1 mRNA transcripts including exon 73 and excluding exon 73, in HPF cells that carry an unaltered COL7A1 sequence. A dose-response was done with mh-AON1, with 50, 100 and 200 nm. FIG. 8A shows the results after 24 h. FIG. 8B shows the results after 40 h transfection with the oligonucleotide. Black bars represent the full length product while the grey bars represent the transcript Δ73.

Figure 9:
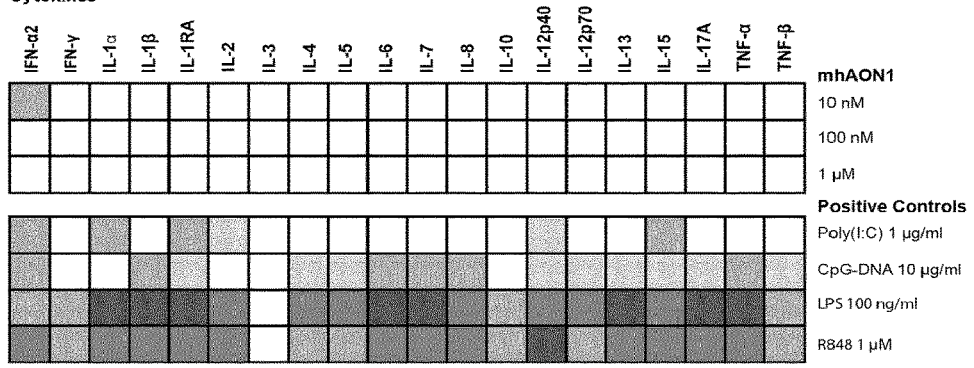
Figure 9:
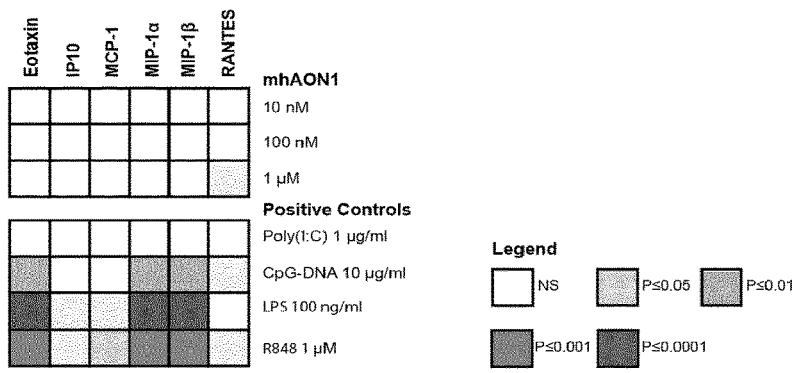
Figure 9:
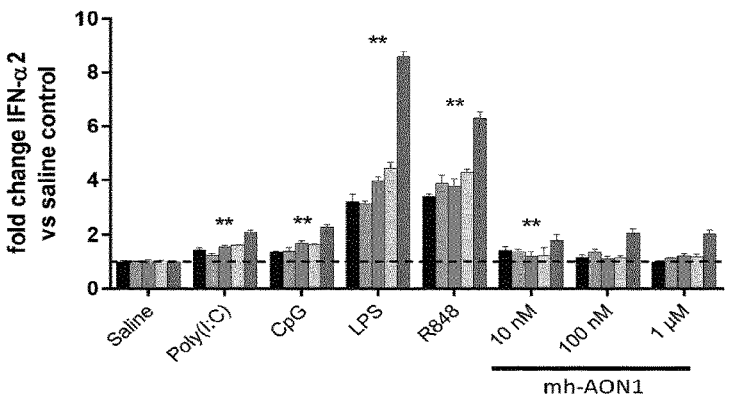
Figure 9:
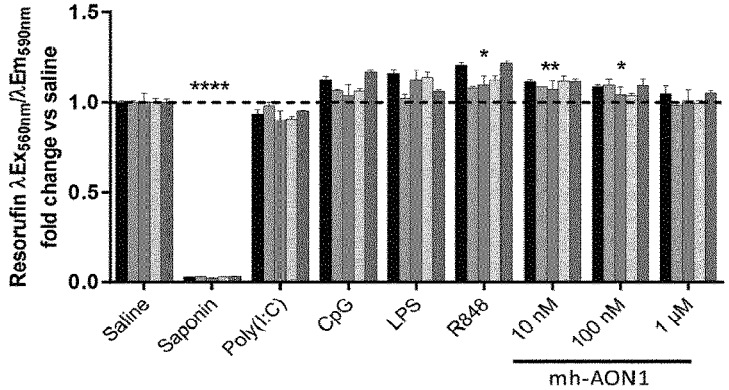

FIG. 9 shows the results of the immunogenicity and immunotoxicity assessment of mh-AON1 in human PBMC. (a) Heat map depicting the significance levels of cytokine concentrations in culture supernatant after 24 h stimulation of human PBMC with mh-AON1 (10 nM, 100 nM or 1 µM) or the positive controls Poly(I:C) (1 µg/ml), CpG (10 µg/ml), LPS (100 ng/ml) and R848 (1 µM) compared to saline-treated human PBMC. Every square shows the reached significance level per treatment condition (geometric mean of the five human donor with triplicate measurements each) for each measured cytokine. (b) Fold change of IFN-α2 concentration in culture supernatant after 24 hrs stimulation of PBMC with mh-AON1 or the positive controls compared to saline-treated PBMC. Bars depict the mean with SEM of triplicate measurements per human donor (in different grey tones). The dotted line at 1 depicts the relative cytokine concentration of the saline treated PMBCs. P-values in (a) and (b) were determined using the Friedman test with Dunn's post-hoc test (c) Relative number of viable PBMC expressed as fold change of Resorufin fluorescence compared to saline treated PBMC after 24 h exposure to mh-AON1 or the positive controls. Viable cell assessment was performed using the CellTiter-Blue kit. For all individual biological replicates, fold changes were calculated by normalizing measured RFU against geometric mean of corresponding triplicate saline control. Results are shown per individual donor as the mean+SEM of the triplicate fold change, normalized against the mean of its corresponding saline control (dotted line). Repeated measures One-way ANOVA with Dunnett test for multiple corrections (compared to saline) was performed. (*$P<0.05$, $P\leq0.01$, **$P<0.001$).

Figure 10:
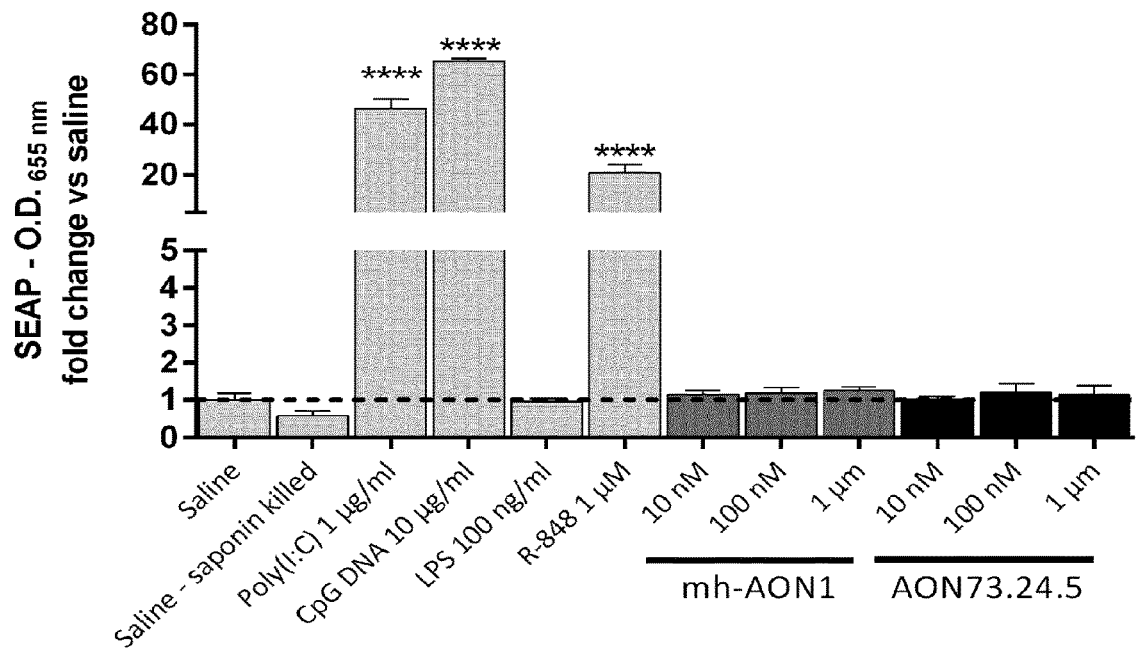
Figure 10:
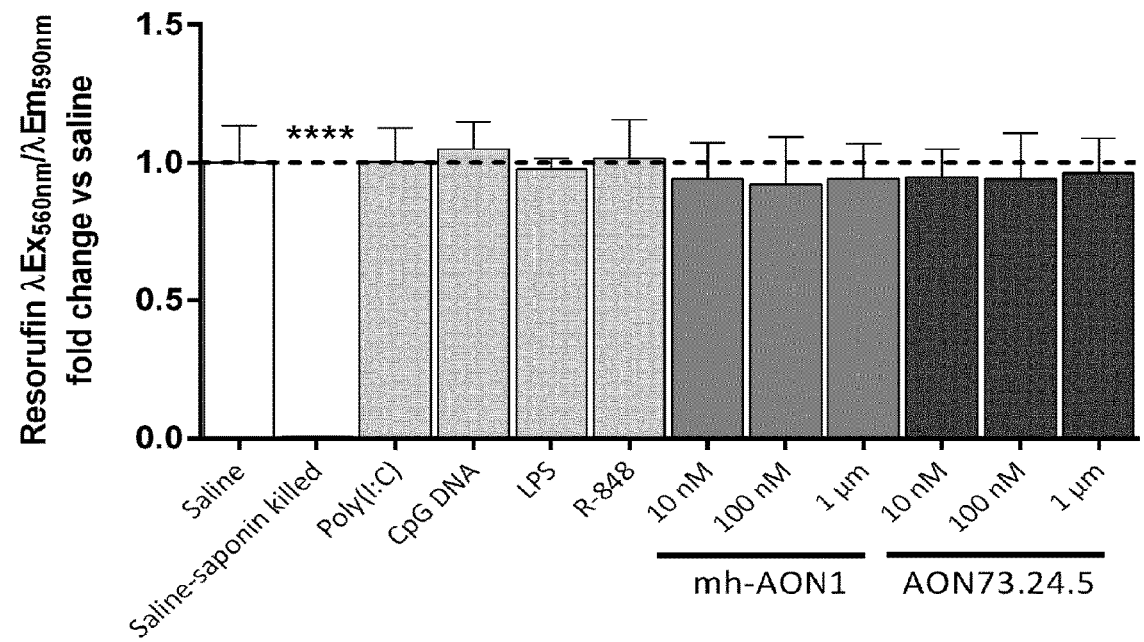

FIG. 10 shows the results of the immunogenicity and immunotoxicity assessment of mh-AON1 and AON73.24.5 in human Ramos-Blue cells. (a) NF-kB/AP-1 activation in Ramos-Blue cells after 24 h incubation with mh-AON1 or AON73.24.5 (at several concentrations) and the TLR agonists Poly(I:C) (1 µg/ml), CpG (10 µg/ml), LPS (100 ng/ml) and R848 (1 µM). (b) Relative number of viable Ramos-Blue cells expressed as fold change of resorufin fluorescence compared to saline treated Ramos-Blue cells after 24 hrs exposure to mh-AON1, AON73.45.5 or the positive controls. Viable cell assessment was performed using the CellTiter-Blue kit. For all individual biological replicates, fold changes were calculated by normalizing measured O.D (in a) or RFU (in b) against geometric mean of corresponding triplicate saline control. Results are shown per as the mean+SEM of the triplicate fold change, normalized against the mean of its corresponding saline control (dotted line). Repeated measures One-way ANOVA with Dunnett test for multiple corrections (compared to saline) was performed on the fold change values. (****$P<0.0001$).

DETAILED DESCRIPTION OF THE INVENTION

Surprisingly, it has now been found by the inventors of the present invention that antisense oligonucleotides can be designed that fulfill the requirements for an AON to develop them into therapeutics to treat human disease, in particular dystrophic epidermolysis bullosa (DEB).

Although AON 73.3 disclosed in WO2013/053819 appears to be satisfactory in terms of reducing exon 73 inclusion in the COL7A1 mRNA, this oligonucleotide is unnecessarily long with its length of 30 nt, which is less preferred from a manufacturability, CMC and cost of goods point of view. Moreover, the INSERM oligonucleotides contain multiple CpG repeats, which is less preferred from an immunogenicity standpoint. It is known that CpGs, especially repeats thereof, interact with the TLR9 receptor, thereby causing an immune response in the treated individual which may harm performance and/or cause harm to the tissues treated with the oligonucleotide.

Preferred AONs of the invention are less than 25, preferably less than 24, nucleotides in length, capable of preventing, or at least reducing, inclusion of exon 73 into the COL7A1 mRNA with high efficiency and, compared to the prior art, have fewer (and preferably no) structures or sequences that might hamper functionality.

The shortened mRNA, lacking the entire exon 73 as a result of treatment using AONs of the invention, will be translated into a shorter but functional COL VII protein.

The AONs of the invention preferably contain no more than two (preferably only one, or even none) CpG sequence(s) and/or range in length between 16 and 24 nucleotides, while achieving exon skipping efficiencies of more than 60% (e.g. more than 70%, ideally more than 75% or 80%, preferably more than 85%, and still more preferably more than 90%) as measured in HeLa cells.

In a different aspect of the invention, AONs have been designed capable of annealing to an 8-mer motif that was, until now, not recognized as being important in selection of the 5' splice acceptor site flanking exon 73. It is postulated that this 8-mer motif is a previously overlooked exonic splicing enhancer (ESE), that may be targeted to prevent, or at least reduce, exon 73 inclusion into the COL7A1 mRNA. The inventors of the present invention used a microwalk technique to determine the location of this newly recognized putative ESE, using AONs capable of annealing to the entire motif or part of the motif, designing different AONs that are progressively truncated to shorten the overlap with this motif until exon skipping is lost entirely. By so doing, the inventors identified a 5'-UUUCCUGG-3' motif (SEQ ID NO: 4) in the 5'-region of exon 73 (see FIG. 1) that forms an excellent new target for AONs to bring about prevention, or at least reduction, of exon 73 inclusion into the COL7A1 mRNA.

In a further embodiment of the invention, an AON is disclosed which is capable of efficiently preventing, or at least reducing, exon 73 inclusion in the COL7A1 mRNA in both mice and humans. This AON (m-h AON1) is fully complementary to the pre-mRNA target in both mice and humans. This AON has as advantage that it can be used to perform proof of concept studies and toxicology studies in mice using the exact same molecule as the one that will eventually be developed for therapeutic use in humans.

None of the AONs according to the invention appear to produce intermediate bands; only bands corresponding to the wt mRNA or bands corresponding to a full exon 73 less mRNA appear to be generated in cells treated with AONs according to the invention.

A further preferred property of AONs according to the invention is that they do not contain G-tetrads or multiple G's (3 or more consecutive guanosines), thereby avoiding problems associated with multiplex formation and/or solubility.

Table 1 shows for each AON the skipping efficiency of exon 73 in HeLa cells, the nucleotide sequence and SEQ ID NO of preferred AONs according to the invention (AON1-AON25 and m-hAON1), of the AONs used in the microwalk to identify the new ESE-motif (AON26-30), and of truncated versions of the AONs found to bind this ESE-motif which lack undesirable structures such as G-tetrads (AON24.1 to 24.5) while still displaying satisfactory exon skipping efficiencies. Further details about the AONs, their efficacy in other cells, and comparison to prior art AONs, are given in Example 1.

TABLE 1

Efficiency of exon 73 exclusion from mRNA. HPF and HeLa cells were treated for 24 hours with 100 nm AON.

| | HeLa | AON sequence 5'-3' | SEQ ID NO |
|---|---|---|---|
| AON1 | 86% | UCUCCAGGAAAGCCGAUGGGGCCC | 5 |
| AON2 | 85% | AGCCCGCGUUCUCCAGGAAAGCCGA | 6 |
| AON3 | 92% | GUCGCCCUUCAGCCCGCGUUCUCCA | 7 |
| AON4 | 83% | ACGGUCGCCCUUCAGCCCGCGUU | 8 |
| AON5 | 3% | CCCCUGAGGGCCAGGGUCUCCACGG | 9 |
| AON6 | 0% | CAGACCAGGUGGCCCCUGAGGGCCA | 10 |
| AON7 | 0% | CCAAGGGCCAGACCAGGUGGCCCC | 11 |
| AON8 | 0% | CCAGACCAGGUGGCCCCUGAGGGCC | 12 |
| AON9 | 0% | UCUCCCAAGGGCCAGACCAGG | 13 |
| AON10 | 0% | GGAAGGCCCGGGGGGGCCCCUCUC | 14 |
| AON11 | 6% | CCGGCAAGGCCGGAAGGCCCGGGG | 15 |
| AON12 | 0% | AGGCUUUCCAGGCUCCCCGGCAAG | 16 |
| AON13 | 2% | CGGGAAUACCAGGCUUUCCAGGCU | 17 |
| AON14 | 25% | UGCCUGGGAGCCCGGGAAUACCA | 18 |
| AON15 | 8% | CCCACACCCCCAGCCCUGCCUGGG | 19 |
| AON16 | 0% | CCUCUCCCACACCCCCAGCCCU | 20 |
| AON17 | 9% | UCUCUCCUGGCCUUCCUGCCUCU | 21 |
| AON18 | 13% | CACCCUCUCUCCUGGCCUUCCU | 22 |
| AON19 | 7% | CCAGCCUCACCCUCUCUCCUGG | 23 |
| AON20 | 100% | CUCCAGGAAAGCCGAUGGGGCCC | 24 |
| AON21 | 89% | UCCAGGAAAGCCGAUGGGGCCC | 25 |
| AON22 | 85% | CCAGGAAAGCCGAUGGGGCCC | 26 |
| AON23 | 83% | CUCCAGGAAAUCCGAUGGGGCCCu | 27 |
| AON24 | 93% | UCCAGGAAAGCCGAUGGGGCCcug | 28 |
| AON24.1 | 73% | UCCAGGAAAGCCGAUGGG | 39 |
| AON24.2 | 88% | UCCAGGAAAGCCGAUGG | 40 |
| AON24.3 | 79% | UCCAGGAAAGCCGAUG | 41 |
| AON24.4 | 86% | CUCCAGGAAAGCCGAUGG | 42 |
| AON24.5 | 89% | UCUCCAGGAAAGCCGAUG | 43 |
| AON25 | 92% | CCAGGAAAGCCGAUGGGGCCcugc | 29 |
| AON26 | 49% | AGGAAAGCCGAUGGGGCCcugcag | 30 |
| AON27 | 37% | GAAAGCCGAUGGGGCCcugcagga | 31 |
| AON28 | 47% | AAGCCGAUGGGGCCcugcaggagu | 32 |
| AON29 | 0% | GCCGAUGGGGCCcugcaggagugg | 33 |
| AON30 | 7% | GAUGGGGCCcugcaggaguggaa | 34 |
| mh-AON 1 | 91% | CGUUCUCCAGGAAAGCCGAUG | 35 |

According to one embodiment, an antisense oligonucleotide is provided that is capable of preventing or reducing exon 73 inclusion into the mammalian (preferably human) COL7A1 mRNA, when said mRNA is produced by splicing from a pre-mRNA in a mammalian cell characterized in that the oligonucleotide's sequence has at least one of properties (a) and/or (b): (a) it includes at most two CpG sequences; and/or (b) it has a length of no more than 24 nucleotides. For property (a), the oligonucleotide preferably includes no more than one CpG sequence, and may include only one.

According to another embodiment, an antisense oligonucleotide is provided that is capable of preventing or reducing exon 73 inclusion into the mammalian (preferably human) COL7A1 mRNA, when said mRNA is produced by splicing from a pre-mRNA in a mammalian cell, characterized in that the oligonucleotide is capable of annealing to the sequence motif 5'-UUUCCUGG-3' (SEQ ID NO: 4) in the 5' upstream part of exon 73 (FIG. 1). Without wishing to be bound by theory, this motif is postulated to represent a SRp40/SC35 binding exonic splicing enhancer (ESE) element. The AONs according to this embodiment are preferably characterized in that the oligonucleotide's sequence has one or both of properties (a) and/or (b) as discussed above. In order to have optimal effect the oligonucleotide should anneal to the entire 8-mer motif; if exon skipping efficiencies below 60% would be acceptable for any particular scenario then annealing to the 6 or 7 most 5' nucleotides of the 8-mer motif can be acceptable.

Further preferred AONs according to the invention are those wherein feature (a) is characterized by that the oligonucleotide includes no more than one CpG, and/or feature (b) is characterized in that the oligonucleotide has a length of no more than 24 nucleotides, preferably between 12 and 24 nucleotides, more preferably between 16 and 24 nucleotides, such as 16, 17, 18, 19, 20, 21, 22, 23 or 24 nucleotides still more preferably less than 23 nucleotides, still more preferably between 16 and 23 nucleotides, such as 16, 17, 18, 19, 20, 21, 22, 23 nucleotides. According to most preferred embodiments of the invention, the oligonucleotides are characterized in that they have both properties (a) at most two CpG sequences, preferably no more than one, such as one CpG and (b) a length of no more than 24 nucleotides, preferably between 12 and 24 nucleotides, more preferably between 16 and 24 nucleotides, such as 16, 17, 18, 19, 20, 21, 22, 23 or 24 nucleotides, still more preferably less than 23 nucleotides, still more preferably between 16 and 23 nucleotides, such as 16, 17, 18, 19, 20, 21, 22, 23 nucleotides.

An optional further feature of AONs according to the invention is that their sequence lacks a stretch of 3 or more consecutive guanosines.

Specific preferred AONs of the invention have the nucleotide sequences AON1, AON2, AON3, AON4, AON20, AON21, AON22, AON23, AON24, AON24.1, AON24.2, AON24.3, AON24.3, AON.24.4, AON.24.5, AON25 and mh-AON1 as disclosed in Table 1 above. More preferably for these oligo's, all ribose moieties are 2'-O-methylated and substantially all internucleosidic linkages are phosphorothioates.

In all embodiments of the present invention, the terms "preventing, or at least reducing, exon inclusion" and "exon skipping" are synonymous. In respect of COL7A1, "preventing, or at least reducing, exon inclusion" or "exon skipping" are to be construed as the exclusion of exon 73 (SEQ ID NO: 1, or allelic forms thereof) from the human COL7A1 mRNA (see FIG. 1). The term exon skipping is herein defined as the induction within a cell of a mature mRNA that does not contain a particular exon that would be present in the mature mRNA without exon skipping. Exon skipping is achieved by providing a cell expressing the pre-mRNA of said mature mRNA with a molecule capable of interfering with sequences such as, for example, the splice donor or splice acceptor sequence required for allowing the biochemical process of splicing, or with a molecule that is capable of interfering with an exon inclusion signal required for recognition of a stretch of nucleotides as an exon to be included in the mature mRNA; such molecules are herein referred to as exon skipping molecules.

The term pre-mRNA refers to a non-processed or partly-processed precursor mRNA that is synthesized from a DNA template in a cell by transcription.

The term "antisense oligonucleotide" is understood to refer to a nucleotide sequence which is complementary to a target nucleotide sequence in a pre-mRNA molecule, hnRNA (heterogeneous nuclear RNA) or mRNA molecule, so that it is capable of annealing with its corresponding target sequence.

The term "complementary" as used herein includes "fully complementary" and "substantially complementary", meaning there will usually be a degree of complementarity between the oligonucleotide and its corresponding target sequence of more than 80%, preferably more than 85%, still more preferably more than 90%, most preferably more than 95%. For example, for an oligonucleotide of 20 nucleotides in length with one mismatch between its sequence and its target sequence, the degree of complementarity is 95%.

The degree of complementarity of the antisense sequence is preferably such that a molecule comprising the antisense sequence can anneal to the target nucleotide sequence in the RNA molecule under physiological conditions, thereby facilitating exon skipping. It is well known to a person having ordinary skill in the art, that certain mismatches are more permissible than others, because certain mismatches have less effect on the strength of binding, as expressed in terms of melting temperature or Tm, between AON and target sequence, than others. Certain non-complementary base pairs may form so-called "wobbles" that disrupt the overall binding to a lesser extent than true mismatches. The length of the AON also plays a role in the strength of binding, longer AONs having higher melting temperatures as a rule than shorter AONs, and the G/C content of an oligonucleotide is also a factor that determines the strength of binding, the higher the G/C content the higher the melting temperature for any given length. Certain chemical modifications of the nucleobases or the sugar-phosphate backbone, as contemplated by the present invention, may also influence the strength of binding, such that the degree of complementarity is only one factor to be taken into account when designing an oligonucleotide according to the invention.

The presence of a CpG or multitude (two or more) of CpGs in an oligonucleotide is usually associated with an increased immunogenicity of said oligonucleotide (Dorn & Kippenberger, 2008). This increased immunogenicity is undesired since it may induce damage of the tissue to be treated, i.e. the skin (dermis and/or epidermis).

The invention allows designing an oligonucleotide with acceptable RNA binding kinetics and/or thermodynamic properties. The RNA binding kinetics and/or thermodynamic properties are at least in part determined by the melting temperature of an oligonucleotide (Tm; calculated with the oligonucleotide properties calculator (available on the world wide web at www.unc.edu/~cail/biotool/oligo/index.html) for single stranded RNA using the basic Tm and the nearest neighbor models), and/or the free energy of the AON-target exon complex (using RNA structure version 4.5). If a Tm is too high, the oligonucleotide is expected to be less specific. An acceptable Tm and free energy depend on the sequence of the oligonucleotide, the chemistry of the backbone (phosphodiester, phosphorothioate, phosphoramidate, peptide-nucleic acid, etc.), the nature of the sugar moiety (ribose, deoxyribose, substituted ribose, intramolecular bridge) and chemical modification of the nucleobase. Therefore, the range of Tm can vary widely. In accordance with one aspect of the invention, new AONs are provided according to the invention by microwalking the 5' region of exon 73 with AONs. Thus, a novel 8 nucleotide motif (a putative ESE) has been identified that forms a suitable target to design AONs according to the invention.

The length of the oligo selected by the present inventors was between 16 and 24 nucleotides, but a different length is also possible. It is preferred to have a length that is long enough to allow for a stable interaction with the target RNA and specificity for the target sequence but not longer than necessary, as longer oligonucleotides are more expensive to manufacture and are more complex from an analytical point of view. The 5' region of exon 73 may be probed for efficient exon skipping molecules, by making a series of overlapping oligonucleotides that are tested in an in vitro assay for their efficacy of exon skipping—as exemplified in the examples. The AONs that establish a satisfactory exon skipping efficacy are then further selected on the basis of the manufacturability, immunogenicity and other usability criteria provided herein.

The opposite strategy is also possible. In accordance with this strategy, the oligo's are first designed based on the manufacturability, immunogenicity and other usability criteria provided by the present invention, and are then tested for exon skipping efficiency. A functional activity of said oligonucleotide is preferably to induce the skipping of exon 73 (SEQ ID NO: 1) to a certain extent and/or at least decreasing the production of an exon 73 containing mRNA, thereby increasing the production of a shorter than wild-type yet functional collagen protein.

The exon skipping percentage or efficiency may be calculated by determining the concentration of wild-type band amplified, divided by the concentration of the shortened (exon 73-free) band amplified, after a given number of PCR cycles, times 100%, for any given primer set, provided the number of cycles is such that the amplification is still in the exponential phase. Quantification can be performed using the Bioanalyzer DNA1000 apparatus Preferred AONs according to the invention are those showing a skipping percentage of more than 70% in AON-treated cells compared to non-treated cells, more preferably more than 80%, still more preferably more than 90%, as measured by RT-PCR analysis.

Preferably, an AON according to the invention, which comprises a sequence that is complementary to a nucleotide sequence as shown in SEQ ID NO: 1 is such that the complementary part is at least 80%, more preferably at least 90%, still more preferably at least 95%, most 100% complementary to the target sequence. It is thus not absolutely required that all the bases in the region of complementarity are capable of pairing with bases in the opposing strand. For instance, when designing the oligonucleotide one may want to incorporate for instance a residue that does not base pair with the base on the complementary strand. Mismatches may, to some extent, be allowed, if under the circumstances in the cell, the stretch of nucleotides is sufficiently capable of hybridizing to the complementary part. In this context, "sufficiently" means that the AONs according to the invention are capable of inducing exon skipping of exon 73. Skipping the targeted exon may conveniently be assessed by RT-PCR. The complementary regions are preferably designed such that, when combined, they are specific for the exon in the pre-mRNA. Such specificity may be created with various lengths of complementary regions as this depends on the actual sequences in other (pre-)mRNA molecules in the system. The risk that the oligonucleotide also will be able to hybridize to one or more other pre-mRNA molecules decreases with increasing size of the oligonucleotide, while the length should not be too long to create problems with manufacturability, purification and/or analytics.

It is clear that oligonucleotides comprising mismatches in the region of complementarity but that retain the capacity to hybridize and/or bind to the targeted region(s) in the pre-mRNA, can be used in the present invention. However, preferably at least the complementary parts do not comprise such mismatches as these typically have a higher efficiency and a higher specificity, than oligonucleotides having such mismatches in one or more complementary regions. It is thought, that higher hybridization strengths, (i.e. increasing number of interactions with the opposing strand) are favorable in increasing the efficiency of the process of interfering with the splicing machinery of the system. Preferably, the complementarity is from 90% to 100%. In general this allows for 1 or 2 mismatch(es) in an oligonucleotide of 20 nucleotides.

An exon skipping molecule of the invention is preferably an (antisense) oligonucleotide, which is complementary to SEQ ID NO: 1.

Preferably, the length of the complementary part of the oligonucleotide is the same as the length of the oligonucleotide, meaning there are no 5' or 3' ends of the oligo that do not form a base pair with the target RNA. Thus a preferred length for an oligonucleotide of the invention is 24 nucleotides or less e.g. 12, 13, 14, 15, 16, 17, 18, 19, 20, 21, 22, 23 or 24 nucleotides.

Particularly good results have been obtained with AONs having a length between 16 and 24 nucleotides.

An exon skipping molecule according to the invention may contain one of more DNA residues (consequently a RNA "u" residue will be a "t" residue as DNA counterpart), or one or more RNA residues, and/or one or more nucleotide analogues or equivalents, as will be further detailed herein below. SEQ ID NOs: 5-35 & 39-43 are RNA sequences, but the invention also encompasses each of these sequences in DNA form, and also DNA/RNA hybrids of these sequences.

It is preferred that an exon skipping molecule of the invention comprises one or more residues that are modified to increase nuclease resistance, and/or to increase the affinity of the antisense oligonucleotide for the target sequence. Therefore, in a preferred embodiment, the antisense nucleotide sequence comprises at least one nucleotide analogue or equivalent, wherein a nucleotide analogue or equivalent is defined as a residue having a modified base, and/or a modified backbone, and/or a non-natural internucleoside linkage, or a combination of these modifications.

In a preferred embodiment, the nucleotide analogue or equivalent comprises a modified backbone. Examples of such backbones are provided by morpholino backbones, carbamate backbones, siloxane backbones, sulfide, sulfoxide and sulfone backbones, formacetyl and thioformacetyl backbones, methyleneformacetyl backbones, riboacetyl backbones, alkene containing backbones, sulfamate, sulfonate and sulfonamide backbones, methyleneimino and methylenehydrazino backbones, and amide backbones. Phosphorodiamidate morpholino oligomers are modified backbone oligonucleotides that have previously been investigated as antisense agents. Morpholino oligonucleotides have an uncharged backbone in which the deoxyribose sugar of DNA is replaced by a six membered ring and the phosphodiester linkage is replaced by a phosphorodiamidate linkage. Morpholino oligonucleotides are resistant to enzymatic degradation and appear to function as antisense agents by arresting translation or interfering with pre-mRNA splicing rather than by activating RNase H. Morpholino oligonucleotides have been successfully delivered to tissue culture cells by methods that physically disrupt the cell membrane, and one study comparing several of these methods found that scrape loading was the most efficient method of delivery; however, because the morpholino backbone is uncharged, cationic lipids are not effective mediators of morpholino oligonucleotide uptake in cells.

According to one embodiment of the invention the linkage between the residues in a backbone do not include a phosphorus atom, such as a linkage that is formed by short chain alkyl or cycloalkyl internucleoside linkages, mixed heteroatom and alkyl or cycloalkyl internucleoside linkages, or one or more short chain heteroatomic or heterocyclic internucleoside linkages.

In accordance with this embodiment, a preferred nucleotide analogue or equivalent comprises a Peptide Nucleic Acid (PNA), having a modified polyamide backbone (Nielsen, et al. (1991) Science 254, 1497-1500). PNA-based molecules are true mimics of DNA molecules in terms of base-pair recognition. The backbone of the PNA is composed of N-(2-aminoethyl)-glycine units linked by peptide bonds, wherein the nucleobases are linked to the backbone by methylene carbonyl bonds. An alternative backbone comprises a one-carbon extended pyrrolidine PNA monomer (Govindaraju and Kumar (2005) Chem. Commun, 495-497). Since the backbone of a PNA molecule contains no charged phosphate groups, PNA-RNA hybrids are usually more stable than RNA-RNA or RNA-DNA hybrids, respectively (Egholm et al. (1993) Nature 365, 566-568).

According to another embodiment of the invention, the backbone comprises a morpholino nucleotide analog or equivalent, in which the ribose or deoxyribose sugar is replaced by a 6-membered morpholino ring. A most preferred nucleotide analog or equivalent comprises a phosphorodiamidate morpholino oligomer (PMO), in which the ribose or deoxyribose sugar is replaced by a 6-membered morpholino ring, and the anionic phosphodiester linkage between adjacent morpholino rings is replaced by a non-ionic phosphorodiamidate linkage.

In yet a further embodiment, a nucleotide analogue or equivalent of the invention comprises a substitution of one of the non-bridging oxygens in the phosphodiester linkage. This modification slightly destabilizes base-pairing but adds significant resistance to nuclease degradation. A preferred nucleotide analogue or equivalent comprises phosphorothioate, chiral phosphorothioate, phosphorodithioate, phosphotriester, aminoalkylphosphotriester, H-phosphonate, methyl and other alkyl phosphonate including 3'-alkylene phosphonate, 5'-alkylene phosphonate and chiral phosphonate, phosphinate, phosphoramidate including 3'-amino phosphoramidate and aminoalkylphosphoramidate, thionophosphoramidate, thionoalkylphosphonate, thionoalkylphosphotriester, selenophosphate or boranophosphate.

A further preferred nucleotide analogue or equivalent of the invention comprises one or more sugar moieties that are mono- or disubstituted at the 2', 3' and/or 5' position such as a —OH; —F; substituted or unsubstituted, linear or branched lower (C1-C10) alkyl, alkenyl, alkynyl, alkaryl, allyl, or aralkyl, that may be interrupted by one or more heteroatoms; O-, S-, or N-alkyl; O-, S-, or N-alkenyl; O-, S- or N-alkynyl; O-, S-, or N-allyl; O-alkyl-O-alkyl, -methoxy, -aminopropoxy; methoxyethoxy; -dimethylaminooxyethoxy; and -dimethylaminoethoxyethoxy. The sugar moiety can be a furanose or derivative thereof, or a deoxyfuranose or derivative thereof, preferably ribose or derivative thereof, or deoxyribose or derivative of. A preferred derivatized sugar moiety comprises a Locked Nucleic Acid (LNA), in which the 2'-carbon atom is linked to the 3' or 4' carbon atom of the sugar ring thereby forming a bicyclic sugar moiety. A preferred LNA comprises 2'-0,4'-C-ethylene-bridged nucleic acid (Morita et al. 2001. Nucleic Acid Res Supplement No. 1: 241-242). These substitutions render the nucleotide analogue or equivalent RNase H and nuclease resistant and increase the affinity for the target RNA.

It is understood by a skilled person that it is not necessary for all internucleosidic linkages in an antisense oligonucleotide to be modified. For example, some internucleosidic linkages may be unmodified, whereas other internucleosidic linkages are modified. AONs comprising a backbone consisting of one form of (modified) internucleosidic linkages, multiple forms of (modified) internucleosidic linkages, uniformly or non-uniformly distributed along the length of the AON are all encompassed by the present invention. In addition, any modality of backbone modification (uniform, non-uniform, mono-form or pluriform and all permutations thereof) may be combined with any form or of sugar or nucleoside modifications or analogues mentioned below.

An especially preferred backbone for the AONs according to the invention is a uniform (all) phosphorothioate (PS) backbone.

In another embodiment, a nucleotide analogue or equivalent of the invention comprises one or more base modifications or substitutions. Modified bases comprise synthetic and natural bases such as inosine, xanthine, hypoxanthine and other -aza, deaza, -hydroxy, -halo, -thio, thiol, -alkyl, -alkenyl, -alkynyl, thioalkyl derivatives of pyrimidine and purine bases that are or will be known in the art.

It is understood by a skilled person that it is not necessary for all positions in an antisense oligonucleotide to be modified uniformly. In addition, more than one of the aforementioned analogues or equivalents may be incorporated in a single antisense oligonucleotide or even at a single position within an antisense oligonucleotide. In certain embodiments, an antisense oligonucleotide of the invention has at least two different types of analogues or equivalents.

According to another embodiment AONs according to the invention comprise a 2'-O (preferably lower) alkyl phosphorothioate antisense oligonucleotide, such as 2'-O-methyl modified ribose (RNA), 2'-O-methoxyethyl modified ribose, 2'-O-ethyl modified ribose, 2'-O-propyl modified ribose, and/or substituted derivatives of these modifications such as halogenated derivatives.

An effective and preferred antisense oligonucleotide format according to the invention comprises 2'-O-methyl modified ribose moieties with a phosphorothioate backbone, preferably wherein substantially all ribose moieties are 2'-O-methyl and substantially all internucleosidic linkages are phosphorothioate linkages.

It will also be understood by a skilled person that different antisense oligonucleotides can be combined for efficiently skipping of exon 73 of the COL7A1 gene. A combination of two antisense oligonucleotides may be used in a method of the invention, such as two antisense oligonucleotides, three different antisense oligonucleotides, four different antisense oligonucleotides, or five different antisense oligonucleotides targeting the same or different regions of exon 73 (FIG. 1), as long as at least one AON is one according to the invention.

An antisense oligonucleotide can be linked to a moiety that enhances uptake of the antisense oligonucleotide in cells, preferably skin cells. Examples of such moieties are cholesterols, carbohydrates, vitamins, biotin, lipids, phospholipids, cell-penetrating peptides including but not limited to antennapedia, TAT, transportan and positively charged amino acids such as oligoarginine, poly-arginine, oligolysine or polylysine, antigen-binding domains such as provided by an antibody, a Fab fragment of an antibody, or a single chain antigen binding domain such as a camelid single domain antigen-binding domain.

An exon skipping molecule according to the invention may be a naked (gymnotic) antisense oligonucleotide or in the form of a conjugate or expressed from a vector (vectored AON). The exon skipping molecule may be administrated using suitable means known in the art. When the exon skipping molecule is a vectored AON, it may for example be provided to an individual or a cell, tissue or organ of said individual in the form of an expression vector wherein the expression vector encodes a transcript comprising said oligonucleotide. The expression vector is preferably introduced into a cell, tissue, organ or individual via a gene delivery vehicle, such as a viral vector. In a preferred embodiment, there is provided a viral-based expression vector comprising an expression cassette or a transcription cassette that drives expression or transcription of an exon skipping molecule as identified herein. Accordingly, the present invention provides a viral vector expressing an exon skipping molecule according to the invention when placed under conditions conducive to expression of the exon skipping molecule. A cell can be provided with an exon skipping molecule capable of interfering with sequences essential for, or at least conducive to, exon 73 inclusion, such that such interference prevents, or at least reduces, exon 73 inclusion into the COL7A1 mRNA, for example by plasmid-derived antisense oligonucleotide expression or viral expression provided by adenovirus- or adeno-associated virus-based vectors. Expression may be driven by a polymerase III promoter, such as a U1, a U6, or a U7 RNA promoter. A preferred delivery vehicle is a viral vector such as an adeno-associated virus vector (AAV), or a retroviral vector such as a lentivirus vector and the like. Also, plasmids, artificial chromosomes, plasmids usable for targeted homologous recombination and integration in the mammalian (preferably human) genome of cells may be suitably applied for delivery of an oligonucleotide as defined herein. Preferred for the current invention are those vectors wherein transcription is driven from PolIII promoters, and/or wherein transcripts are in the form of fusions with U1 or U7 transcripts, which yield good results for delivering small transcripts. It is within the skill of the artisan to design suitable transcripts. Preferred are PolIII driven transcripts. Preferably, in the form of a fusion transcript with an U1 or U7 transcript. Such fusions may be generated as described in the art (e.g. vide: Gorman L et al., 1998 or Suter D et al., 1999).

One preferred antisense oligonucleotide expression system is an adenovirus associated virus (AAV)-based vector. Single chain and double chain AAV-based vectors have been developed that can be used for prolonged expression of antisense nucleotide sequences for highly efficient skipping of COL7A1 exon 73.

A preferred AAV-based vector for instance comprises an expression cassette that is driven by a polymerase III-promoter (Pol III). A preferred Pol III promoter is, for example, a U1, a U6, or a U7 RNA promoter.

The invention therefore also provides a viral-based vector, comprising a Pol III-promoter driven expression cassette for expression of an antisense oligonucleotide of the invention for inducing skipping of COL7A1 exon 73.

An AAV vector according to the present invention is a recombinant AAV vector and refers to an AAV vector comprising part of an AAV genome comprising an encoded exon skipping molecule according to the invention encapsidated in a protein shell of capsid protein derived from an AAV serotype as depicted elsewhere herein. Part of an AAV genome may contain the inverted terminal repeats (ITR) derived from an adeno-associated virus serotype, such as AAV1, AAV2, AAV3, AAV4, AAV5, AAV8, AAV9 and others. Protein shell comprised of capsid protein may be derived from an AAV serotype such as AAV1, 2, 3, 4, 5, 8, 9 and others. A protein shell may also be named a capsid protein shell. AAV vector may have one or preferably all wild type AAV genes deleted, but may still comprise functional ITR nucleic acid sequences. Functional ITR sequences are necessary for the replication, rescue and packaging of AAV virions. The ITR sequences may be wild type sequences or may have at least 80%, 85%, 90%, 95, or 100% sequence identity with wild type sequences or may be altered by for example in insertion, mutation, deletion or substitution of nucleotides, as long as they remain functional. In this context, functionality refers to the ability to direct packaging of the genome into the capsid shell and then allow for expression in the host cell to be infected or target cell. In the context of the present invention a capsid protein shell may be of a different serotype than the AAV vector genome ITR. An AAV vector according to present the invention may thus be composed of a capsid protein shell, i.e. the icosahedral capsid, which comprises capsid proteins (VP1, VP2, and/or VP3) of one AAV serotype, e.g. AAV serotype 2, whereas the ITRs sequences contained in that AAV5 vector may be any of the AAV serotypes described above, including an AAV2 vector. An "AAV2 vector" thus comprises a capsid protein shell of AAV serotype 2, while e.g. an "AAV5 vector" comprises a capsid protein shell of AAV serotype 5, whereby either may encapsidate any AAV vector genome ITR according to the invention.

Preferably, a recombinant AAV vector according to the present invention comprises a capsid protein shell of AAV serotype 2, 5, 8 or AAV serotype 9 wherein the AAV genome or ITRs present in said AAV vector are derived from AAV serotype 2, 5, 8 or AAV serotype 9; such AAV vector is referred to as an AAV2/2, AAV 2/5, AAV2/8, AAV2/9, AAV5/2, AAV5/5, AAV5/8, AAV 5/9, AAV8/2, AAV 8/5, AAV8/8, AAV8/9, AAV9/2, AAV9/5, AAV9/8, or an AAV9/9 vector, respectively.

More preferably, a recombinant AAV vector according to the present invention has tropism for dermal and epidermal cells and comprises a capsid protein shell of AAV serotype 5 or 8. The AAV genome or ITRs present in said vector may be derived from the same or a different serotype, such as AAV serotype 2; such vector is referred to as an AAV 2/5 or AAV 2/8 vector. AAV with a serotype 5 capsid have tropism for dermal and epidermal cells, such as basilar and suprabasilar keratinocytes and dermal fibroblasts. AAV vectors with a type 5 capsid display much higher transduction efficiencies compared to AAV with a type 2 capsid (Keswani et al. Wound Repair Regen. 2012; 20(4): 592-600). Similarly, AAV with a capsid of serotype 8 show tropism towards dermal fibroblasts and (mainly) suprabasilar keratinocytes. Moreover, AAV 2/8 tend to be more efficient in transducing mammalian, preferably human dermal and epidermal cells than AAV 2/5. However, transduction efficiency appears to depend on the timing of administration during wound healing, AAV 2/2 showing higher transduction efficiencies than AAV 2/5 and AAV 2/8 at later time points (Keswani et al., supra).

Hence, AAV 2/2, AAV x/5 and AAV x/8 are preferred AAV to deliver AONs according to the invention and their choice may be determined taking into account the time of administration and the cell types to be targeted. These details can be readily worked out a person skilled in the art, in pre-clinical or clinical studies.

A nucleic acid molecule encoding an exon skipping molecule according to the present invention represented by a nucleic acid sequence of choice is preferably inserted between the AAV genome or ITR sequences as identified above, for example an expression construct comprising an expression regulatory element operably linked to a coding sequence and a 3' termination sequence.

"AAV helper functions" generally refers to the corresponding AAV functions required for AAV replication and packaging supplied to the AAV vector in trans. AAV helper functions complement the AAV functions which are missing in the AAV vector, but they lack AAV ITRs (which are provided by the AAV vector genome). AAV helper functions include the two major ORFS of AAV, namely the rep coding region and the cap coding region or functional substantially identical sequences thereof. Rep and Cap regions are well known in the art, see e.g. Chiorini et al. (1999, J. of Virology, Vol 73(2): 1309-1319) or U.S. Pat. No. 5,139,941, incorporated herein by reference. The AAV helper functions can be supplied on a AAV helper construct, which may be a plasmid. Introduction of the helper construct into the host cell can occur e.g. by transformation, transfection, or transduction prior to or concurrently with the introduction of the AAV genome present in the AAV vector as identified herein. The AAV helper constructs of the invention may thus be chosen such that they produce the desired combination of serotypes for the AAV vector's capsid protein shell on the one hand and for the AAV genome present in said AAV vector replication and packaging on the other hand.

"AAV helper virus" provides additional functions required for AAV replication and packaging. Suitable AAV helper viruses include adenoviruses, herpes simplex viruses (such as HSV types 1 and 2) and vaccinia viruses. The additional functions provided by the helper virus can also be introduced into the host cell via vectors, as described in U.S. Pat. No. 6,531,456 incorporated herein by reference.

Preferably, an AAV genome as present in a recombinant AAV vector according to the present invention does not comprise any nucleotide sequences encoding viral proteins, such as the rep (replication) or cap (capsid) genes of AAV. An AAV genome may further comprise a marker or reporter gene, such as a gene for example encoding an antibiotic resistance gene, a fluorescent protein (e.g. gfp) or a gene encoding a chemically, enzymatically or otherwise detectable and/or selectable product (e.g. lacZ, aph, etc.) known in the art.

A preferred AAV vector according to the present invention is an AAV vector, preferably an AAV2/5, AAV2/8, AAV2/9 or AAV2/2 vector, expressing an exon skipping molecule according to the present invention comprising an antisense oligonucleotide, wherein said antisense oligonucleotide comprises or consists of a sequence selected from the group consisting of: AON1, AON2, AON3, AON4, AON20, AON21, AON22, AON23, AON24, AON24.1, AON24.2, AON24.3, AON24.3, AON.24.4, AON.24.5, AON25 and mh-AON1 as disclosed in Table 1 above.

Improvements in means for providing an individual or a cell, tissue, organ of said individual with an exon skipping molecule according to the invention, are anticipated considering the progress that has already thus far been achieved. Such future improvements may of course be incorporated to achieve the mentioned effect on restructuring of mRNA using a method of the invention. An exon skipping molecule according to the invention can be delivered as is to an individual, a cell, tissue or organ of said individual. When administering an exon skipping molecule according to the invention, it is preferred that the molecule is dissolved in a solution that is compatible with the delivery method.

Gymnotic AONs are readily taken up by most cells in vivo, and usually dissolving the AONs according to the invention in an isotonic (saline) solution will be sufficient to reach the target cells, such as skin (dermis and epidermis) cells. Alternatively, gymnotic AONs of the invention may be formulated using pharmaceutically acceptable excipients, additives, stabilizers, solvents, colorants and the like. In addition, or alternatively, gymnotic AONs may be formulated with any of the transfection aids mentioned below.

Skin (dermis and epidermis) cells can be provided with a plasmid for antisense oligonucleotide expression by providing the plasmid in an aqueous solution, such as an isotonic (saline) solution. Alternatively, a plasmid can be provided by transfection using known transfection agents.

For intravenous, subcutaneous, intramuscular, intrathecal and/or intradermal administration it is preferred that the solution is an isotonic (saline) solution. Particularly preferred in the invention is the use of an excipient or transfection agents that will aid in delivery of each of the constituents as defined herein to a cell and/or into a cell, preferably a skin (dermis and epidermis) cell. Preferred are excipients or transfection agents capable of forming complexes, nanoparticles, micelles, vesicles and/or liposomes that deliver each constituent as defined herein, complexed or trapped in a vesicle or liposome through a cell membrane. Many of these excipients are known in the art. Suitable excipients or transfection agents comprise polyethylenimine (PEI; ExGen500 (MBI Fermentas)), LipofectAMINE™ 2000 (Invitrogen) or derivatives thereof, or similar cationic polymers, including polypropyleneimine or polyethylenimine copolymers (PECs) and derivatives, synthetic amphiphils (SAINT-18), lipofectin™, DOTAP and/or viral capsid proteins that are capable of self-assembly into particles that can deliver each constituent as defined herein to a cell, preferably a skin (dermis or epidermis) cell. Such excipients have been shown to efficiently deliver an oligonucleotide such as antisense nucleic acids to a wide variety of cultured cells, including skin (dermis and epidermis) cells. Their high transfection potential is combined with an acceptably low to moderate toxicity in terms of overall cell survival. The ease of structural modification can be used to allow further modifications and the analysis of their further (in vivo) nucleic acid transfer characteristics and toxicity.

Lipofectin represents an example of a liposomal transfection agent. It consists of two lipid components, a cationic lipid N-[1-(2,3 dioleoyloxy)propyl]-N,N,N-trimethylammonium chloride (DOTMA) (cp. DOTAP which is the methylsulfate salt) and a neutral lipid dioleoylphosphatidylethanolamine (DOPE). The neutral component mediates the intracellular release. Another group of delivery systems are polymeric nanoparticles.

Polycations such like diethylaminoethylaminoethyl (DEAE)-dextran, which are well known as DNA transfection reagent can be combined with butylcyanoacrylate (PBCA) and hexylcyanoacrylate (PHCA) to formulate cationic nanoparticles that can deliver each constituent as defined herein, preferably an oligonucleotide, across cell membranes into cells.

In addition to these common nanoparticle materials, the cationic peptide protamine offers an alternative approach to formulate an oligonucleotide with colloids. This colloidal nanoparticle system can form so called proticles, which can be prepared by a simple self-assembly process to package and mediate intracellular release of an oligonucleotide. The skilled person may select and adapt any of the above or other commercially available alternative excipients and delivery systems to package and deliver an exon skipping molecule for use in the current invention to deliver it for the prevention, treatment or delay of a disease or condition associated with a mutated exon 73 in the COL7A1 gene.

An exon skipping molecule according to the invention could be covalently or non-covalently linked to a targeting ligand specifically designed to facilitate the uptake into the cell (especially a skin (dermis) cell), cytoplasm and/or its nucleus. Such ligand could comprise (i) a compound (including but not limited to peptide(-like) structures) recognizing cell, tissue or organ specific elements facilitating cellular uptake and/or (ii) a chemical compound able to facilitate the uptake in to cells and/or the intracellular release of an oligonucleotide from vesicles, e.g. endosomes or lysosomes.

Therefore, in a preferred embodiment, an exon skipping molecule according to the invention is formulated in a composition or a medicament or a composition, which is provided with at least an excipient and/or a targeting ligand for delivery and/or a delivery device thereof to a cell and/or enhancing its intracellular delivery.

Preferred delivery is through topical administration. As outlined in the accompanying examples such may be through the use of a pharmaceutically acceptable hydrogel, such as Flaminal Hydro®, which is a hydrogel already used in patient care, (2) a hypromellose hydrogel or (3) a carbomer hydrogel. Topical formulations that may be used for the topical delivery of the oligonucleotides of the present invention are:

Creams, either formulated as a water-in-oil or as an oil-in-water emulsion; the latter are more cosmetically and aesthetically acceptable. Examples are Softisan based creams or cetomacrogol creams.

Gels: Solutions or suspensions, which contain a gelling agent that is uniformly distributed throughout the liquid phase. Examples are hydrogels including, but not limited to hypromellose, carbomer and alginate.

Ointments. These usually contain <20% water and >50% hydrocarbons, waxes or polyols as the vehicle. They have a more greasy skin feel than creams.

Pastes: These contain a high percentage of finely dispersed solids with a stiff consistency.

Suspensions, which are liquid preparations that contain solid particles dispensed in a liquid vehicle. Some can be labeled as lotions.

Lotions. These are fluid, somewhat viscous (emulsion) formulations, which share many characteristics with suspensions, low viscosity gels and solutions.

Foams, which are emulsions that have a fluffy consistency, when dispensed.

Sprays, which are fine, small droplets of liquid, generated by a nozzle.

Solutions, which are liquid products that are usually aqueous, but may contain other solvents such as alcohols.

It is to be understood that if a composition comprises an additional constituent such as an adjunct compound defined herein, each constituent of the composition may be formulated in one single combination or composition or preparation. Depending on their identity, the skilled person will know which type of formulation is the most appropriate for each constituent as defined herein. According to one embodiment, the invention provides a composition or a preparation which is in the form of a kit of parts comprising an exon skipping molecule according to the invention and a further adjunct compound as defined herein.

If required, an exon skipping molecule according to the invention or a vector, preferably a viral vector, expressing an exon skipping molecule according to the invention can be incorporated into a pharmaceutically active mixture by adding a pharmaceutically acceptable carrier.

Accordingly, the invention also provides a composition, preferably a pharmaceutical composition, comprising an exon skipping molecule according to the invention, such as gymnotic AON or a viral vector according to the invention and a pharmaceutically acceptable excipient. Such composition may comprise a single exon skipping molecule according to the invention, but may also comprise multiple, distinct exon skipping molecules according to the invention. Such a pharmaceutical composition may comprise any pharmaceutically acceptable excipient, including a carrier, filler, preservative, adjuvant, solubilizer and/or diluent. Such pharmaceutically acceptable carrier, filler, preservative, adjuvant, solubilizer and/or diluent may for instance be found in Remington, 2000. Each feature of said composition has earlier been defined herein.

If multiple distinct exon skipping molecules according to the invention are used, concentration or dose defined herein may refer to the total concentration or dose of all oligonucleotides used or the concentration or dose of each exon skipping molecule used or added. Therefore in one embodiment, there is provided a composition wherein each or the total amount of exon skipping molecules according to the invention used is dosed in an amount ranged from 0.0001 and 100 mg/kg, preferably from 0.001 and 50 mg/kg, still more preferably between 0.01 and 20 mg/kg.

A preferred exon skipping molecule according to the invention, is for the treatment of DEB, or, more generally, a mutated COL7A1 exon 73 related disease or condition of an individual. In all embodiments of the present invention, the term "treatment" is understood to include the prevention and/or delay of the disease or condition. An individual, which may be treated using an exon skipping molecule according to the invention may already have been diagnosed as having DEB or a COL7A1 exon 73 related disease or condition. Alternatively, an individual which may be treated using an exon skipping molecule according to the invention may not have yet been diagnosed, but may be an individual having an increased risk of developing DEB, or a COL7A1 exon 73 related disease or condition in the future given his or her genetic background. A preferred individual is a human being. In a preferred embodiment the mutated COL7A1 exon 73 related disease or condition is DEB.

The present invention further provides an exon skipping molecule according to the invention, such as an AON, or a vector encoding an AON, such as a viral vector, according to the invention, or a composition comprising an AON, or a vector encoding an AON, according to the invention for use as a medicine e.g. for use in treating DEB or, more generally, a mutated COL7A1 exon 73 related disease or condition of an individual (as discussed above).

The invention further provides the use of an exon skipping molecule according to the invention, such as an AON, or a vector encoding an AON, such as a viral vector, according to the invention, or a composition comprising an AON, or a vector encoding an AON, according to the invention in the manufacture of a medicament for treating DEB or, more generally, a mutated COL7A1 exon 73 related disease or condition of an individual (as discussed above).

The invention further provides a method for treating a mammal (preferably a human) carrying in its genome a mutation in exon 73 of the COL7A1 gene causing a disease or disorder, including DEB, comprising administering to the mammal (human) an AON, a (viral) vector, or a pharmaceutical composition of the invention. These patients may suffer, or be at risk of developing DEB or a related disorder. Related disorder, disease or condition also encompasses for example skin cancer (squamous cell carcinoma), or other carcinomas, that may arise as a consequence of a collagen VII deficiency or abnormality in the skin, or other organs of an individual, caused by or associated with a mutation in exon 73 of the COL7A1 gene.

Further embodiments of the invention are AONs, viral vectors encoding AONs, and pharmaceutical compositions comprising AONs according to the invention for use as a medicine to treat a mammal (preferably a human) carrying in its genome a mutation in exon 73 of the COL7A1 gene.

Exon skipping molecules according to the invention may be administered to a patient systemically, locally, topically, through administration that is orally, intraocularly, intrapulmonary, intranasally, intramuscularly, subcutaneously, intradermally, rectally, by swallowing, injecting, inhalation, infusion, spraying, in the form of (aqueous) solutions, suspensions, (oil-in-water) emulsions, ointments, lozenges, pills etcetera.

Dosing may be daily, weekly, monthly, quarterly, once per year, depending on the route of administration and the need of the patient.

Because of the early onset of disease, patients having or at risk of developing a disease, disorder or condition caused by or associated with a mutated exon 73 of the COL7A1 gene, including DEB, may be treated in utero, directly after birth, from 1, 2, 3, 6 months of age, from one year of age, from 3 years of age, from 5 years of age, prior to or after the onset of symptoms, to alleviate, retard development, stop or reverse the symptoms of disease and the like.

A treatment in a use or in a method according to the invention is at least one week, at least one month, at least several months, at least one year, at least 2, 3, 4, 5, 6 years or chronically, even during a patient's entire life. Each exon skipping molecule or exon skipping oligonucleotide or equivalent thereof as defined herein for use according to the invention may be suitable for direct administration to a cell, tissue and/or an organ in vivo of individuals already affected or at risk of developing a mutated COL7A1 exon 73 related disorder, disease or condition, and may be administered directly in vivo, ex vivo or in vitro. The frequency of administration of an oligonucleotide, composition, compound or adjunct compound of the invention may depend on several parameters such as the age of the patient, the nature of the exon skipping molecule (e.g. gymnotic AON or vectored AON, such as AAV or lentiviral vector expressed AONs), the dose, the formulation of said molecule and the like.

Dose ranges of an exon skipping molecule, preferably an oligonucleotide according to the invention are preferably designed on the basis of rising dose studies in clinical trials (in vivo use) for which rigorous protocol requirements exist. An oligonucleotide as defined herein may be used at a dose range from 0.0001 to 100 mg/kg, preferably from 0.01 to 20 mg/kg. The dose and treatment regime may vary widely, depending on many factors, including but not limited to the route of administration (e.g. systemic versus topically), whether the oligo is administered as a gymnotic AON or as vectored AON, the dosing regimen, the age and weight of the patient, and so forth.

In a preferred embodiment, a viral vector, preferably an AAV vector as described earlier herein, as delivery vehicle for a molecule according to the invention, is administered in a dose ranging from $1\times10^9$-$1\times10^{17}$ virus particles per injection, more preferably from $1\times10^{10}$-$1\times10^{14}$, and most preferably $1\times10^{10}$-$1\times10^{12}$ virus particles per injection.

It will be clear to a person having ordinary skill in the art to which this invention pertains, that the details of treatment will need to be established in accordance with and depending on such factors as the sequence and chemistry of the oligonucleotide(s), the route of administration, the formulation, the dose, the dosing regimen, the format (viral vector or gymnotic oligonucleotide), the age and weight of the patient, the stage of the disease and so forth, which may require further non-clinical and clinical investigation.

The invention further provides a method for preventing, or at least reducing, COL7A1 exon 73 inclusion in a cell comprising contacting the cell, preferably a skin cell (dermal fibroblast), with an exon skipping molecule according to the invention, such as a gymnotic AON or a (viral) vector encoding an AON according to the invention, or a composition according to the invention. The features of this aspect are preferably those defined earlier herein.

Unless otherwise indicated each embodiment as described herein may be combined with another embodiment as described herein.

The ability of an exon skipping molecule, such as an AON according to the invention, or a (viral) vector encoding such AON, to prevent, or at least reduce, mutated COL7A1 exon 73 inclusion, when the COL7A1 gene is expressed in a mammalian (preferably human) cell, and to bind to the mammalian (human) COL7A1 pre-mRNA under physiological conditions in a region affecting selection of the 5' splice acceptor, and thereby reduce inclusion of the mutated exon 73 into the COL7A1 mRNA, can be conveniently assessed using the assays disclosed in the experimental section herein. In particular, the exon skipping molecule can be incubated with a cell containing exon 73 (not necessarily mutated) of the COL7A1 gene to assess its ability to reduce production by the cell of mRNA which includes exon 73, e.g. by RT-PCR (which can be quantified using a Bioanalyzer apparatus), as described herein in the experimental section and the examples.

As can be observed in the experimental section and the Examples herein, at the RNA level, addition of various AONs according to the invention targeting exon 73 of the COL7A1 gene indeed resulted in a mRNA lacking exon73, leading to the production of a shorter but functional collagen VII protein.

In fibroblasts (that can be derived from the dermis part of the skin), collagen VII is abundantly expressed. Therefore, it is to be expected that addition of AONs to cultured fibroblasts from DEB patients will result in an increased amount of shortened but functional collagen VII protein that is detectable on Western blot, and as such will demonstrate that AON-based therapy will not only redirect splicing of the COL7A1 mRNA but will also result in restoring collagen VII functionality.

The terms "adenine", "guanine", "cytosine", "thymine", "uracil" and hypoxanthine (the nucleobase in inosine) refer to the nucleobases as such.

The terms adenosine, guanosine, cytidine, thymidine, uridine and inosine, refer to the nucleobases linked to the (desoxy)ribosyl sugar.

The term "nucleoside" refers to the nucleobase linked to the (deoxy)ribosyl sugar.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

The word "include" and all of its tenses and conjugations, is to be read as "include, but is not limited to".

The word "exon skipping molecule" is meant to include gymnotic AONs and vectored AONs, including viral vectors, capable of expressing AONs in a compatible cell.

The word "about" or "approximately" when used in association with a numerical value (e.g. about 10) preferably means that the value may be the given value (of 10) plus or minus 5% of the value.

The sequence information as provided herein should not be so narrowly construed as to require inclusion of erroneously identified bases. The skilled person is capable of identifying such erroneously identified bases and knows how to correct for such errors. In case of sequence errors, the sequence of the polypeptide obtainable by expression of the gene present in SEQ ID NO: 1 containing the nucleic acid sequence coding for the polypeptide should prevail.

EXAMPLES

Example 1: mRNA Analysis of Exon 73

To detect the presence of mRNA of exon 73 in mRNA of COL7A1 extracted mRNA of both HeLa cells and human primary fibroblasts (HPF) were used. Culturing of cells was performed in (a) Dulbecco's Modified Eagle Medium (DMEM) supplemented with 10% fetal bovine serum (FBS) for HeLa, or (b) DMEM AQE supplemented with 20% FBS and 1% natrium pyruvate for HPF cells. All cells were grown at 37° C. 5% $CO_2$.

To determine the exon skip efficiency of described AONs, cells were seeded at 60.000 cells/well (HeLa) into 12-well plates or 150.000 cells/well (PHF) into 6-well plates. After 24 hours of allowing cells growth cells were transfected with 100 nm AON-maxPei complex. RNA isolation was performed with the ReliaPrep™ RNA Cell Miniprep System (Promega), subsequently cDNA was made using the Thermo Scientific Verso kit. PCR for exon 73 was performed with FW primer (5'-GCTGGCATCAAGGCATCT-3'; SEQ ID NO: 51) located at the exon 71-72 boundary and RV primer (5'-TCCTTTCTCTCCCCGTTCTC-3'; SEQ ID NO: 52) located within exon 74. PCR products were visualized with the Bioanalyzer using DNA1000 chips and software Expert 2100 was used for product length analysis.

Skipping efficiencies are shown in Table 2, and FIG. 3 shows lab-on-a-chip results. The AONs according to the invention designated AON1 to AON4, AON20 to AON25 (including AONs 24.1 to 24.5) and m-h AON1 have the best efficiency, with >70% of mRNA having exon 73 removed. The effective AONs target the 5' end of the pre-mRNA.

TABLE 2

Efficiency of exon 73 exclusion from mRNA in HPF and HeLa cells

|  | HPF | HeLa | AON sequence 5'3' | SEQ ID NO | Notes |
|---|---|---|---|---|---|
| ESE73.3 | 82% | 96% | UCUCCA<u>C</u>GGUCGCCCUUCAGCC<u>C</u>GCGUUCU | 37 |  |
| ESE73.7 | 80% | 73% | UCUCCA<u>C</u>GGU<u>C</u>GCCCUUCAGCCC<u>C</u>GC | 38 |  |
| AON1 | 67% | 86% | UCUCCAGGAAAGC<u>C</u>GAUGGGGCCC | 5 |  |
| AON2 | 69% | 85% | AGCC<u>C</u>G<u>C</u>GUUCUCCAGGAAAGC<u>C</u>GA | 6 |  |
| AON3 | 67% | 92% | GU<u>C</u>GCCCUUCAGCC<u>C</u>G<u>C</u>GUUCUCCA | 7 |  |
| AON4 | 91% | 83% | AC<u>G</u>GU<u>C</u>GCCCUUCAGCC<u>C</u>GCGUU | 8 |  |
| AON5 | 10% | 3% | CCCCUGAGGGCCAGGGUCUCCA<u>C</u>GG | 9 |  |
| AON6 | 2% | 0% | CAGACCAGGUGGCCCCUGAGGGCCA | 10 |  |
| AON7 | 4% | 0% | CCAAGGGCCAGACCAGGUGGCCCC | 11 |  |
| AON8 | 0% | 0% | CCAGACCAGGUGGCCCCUGAGGGCC | 12 |  |
| AON9 | 0% | 0% | UCUCCCAAGGGCCAGACCAGG | 13 |  |
| AON10 | 0% | 0% | GGAAGGCC<u>C</u>GGGGGGCCCCUCUC | 14 |  |
| AON11 | 6% | 6% | C<u>C</u>GGCAAGGC<u>C</u>GGAAGGCC<u>C</u>GGGG | 15 |  |
| AON12 | 0% | 0% | AGGCUUUCCAGGCUCCC<u>C</u>GGCAAG | 16 |  |
| AON13 | 0% | 2% | <u>C</u>GGGAAUACCAGGCUUUCCAGGCU | 17 |  |

TABLE 2-continued

Efficiency of exon 73 exclusion from mRNA in HPF and HeLa cells

| | HPF | HeLa | AON sequence 5'3' | SEQ ID NO | Notes |
|---|---|---|---|---|---|
| AON14 | 17% | 25% | UGCCUGGGAGCCCGGGAAUACCA | 18 | |
| AON15 | 8% | 8% | CCCACACCCCCAGCCCUGCCUGGG | 19 | |
| AON16 | 8% | 0% | CCUCUCCCACACCCCCAGCCCU | 20 | |
| AON17 | 9% | 9% | UCUCUCCUGGCCUUCCUGCCUCU | 21 | |
| AON18 | 11% | 13% | CACCCUCUCUCCUGGCCUUCCU | 22 | |
| AON19 | 0% | 7% | CCAGCCUCACCCUCUCUCCUGG | 23 | |
| AON20 | 74% | 100% | CUCCAGGAAAGCCGAUGGGGCCC | 24 | AON1-1N at 3" |
| AON21 | 58% | 89% | UCCAGGAAAGCCGAUGGGGCCC | 25 | AON1-2N at 3" |
| AON22 | 64% | 85% | CCAGGAAAGCCGAUGGGGCCC | 26 | AON1-3N at 3" |
| AON23 | 64% | 83% | CUCCAGGAAAUCCGAUGGGGCCcu | 27 | AON1-N at 3' + 1 at 5' |
| AON24 | 72% | 93% | UCCAGGAAAGCCGAUGGGGCCcug | 28 | AON1-2N at 3' + 2 at 5' |
| AON24.1 | 32% | 73% | UCCAGGAAAGCCGAUGGG | 39 | |
| AON24.2 | 50% | 88% | UCCAGGAAAGCCGAUGG | 40 | |
| AON24.3 | 49% | 79% | UCCAGGAAAGCCGAUG | 41 | |
| AON24.4 | 53% | 86% | CUCCAGGAAAGCCGAUGG | 42 | |
| AON24.5 | 66% | 89% | UCUCCAGGAAAGCCGAUG | 43 | |
| AON25 | 54% | 92% | CCAGGAAAGCCGAUGGGGCCcugc | 29 | AON1-3N at 3' + 3 at 5' |
| AON26 | 22% | 49% | AGGAAAGCCGAUGGGGCCcugcag | 30 | 2N shift towards 5' |
| AON27 | 40% | 37% | GAAAGCCGAUGGGGCCcugcagga | 31 | 4N shift towards 5' |
| AON28 | 20% | 47% | AAGCCGAUGGGGCCcugcaggagu | 32 | 6N shift towards 5' |
| AON29 | 5% | 0% | GCCGAUGGGGCCcugcaggagugg | 33 | 8N shift towards 5' |
| AON30 | 6% | 7% | GAUGGGGCCcugcaggaguggaa | 34 | 11N shift towards 5' |
| AON31 | 0% | 0% | UCCAGGAAAG | 44 | |
| m-hAON 1 | 76% | 91% | CGUUCUCCAGGAAAGCCGAUG | 35 | |
| m-hAON 2 | 0% | 16% | CCUGAGGGCCAGGGUCUCCACG | 36 | |

Two of the AONs that showed satisfactory exon skipping efficiency were truncated by removing a varying number of nucleotides at the 3' end in order to avoid the occurrence of undesirable G-tetrads. These AONs are shown in Table 3.

TABLE 3

Truncated versions of AON24 and AON31

| Name | AONs sequence | SEQ ID NO | RNA binding sequence | SEQ ID NO | length |
|---|---|---|---|---|---|
| AON 24.1 | UCCAGGAAAGCCGAUGGG | 39 | CCCAUCGGCUUUCCUGGA | 45 | 18 |
| 24.2 | UCCAGGAAAGCCGAUGG | 40 | CCAUCGGCUUUCCUGGA | 46 | 17 |
| 24.3 | UCCAGGAAAGCCGAUG | 41 | CAUCGGCUUUCCUGGA | 47 | 16 |
| 24.4 | CUCCAGGAAAGCCGAUGG | 42 | CCAUCGGCUUUCCUGGAG | 48 | 18 |

TABLE 3-continued

Truncated versions of AON24 and AON31

| Name | AONs sequence | SEQ ID NO | RNA binding sequence | SEQ ID NO | length |
|------|---------------|-----------|----------------------|-----------|--------|
| 24.5 | UCUCCAGGAAAGCCGAUG | 43 | CATCGGCTTTCCTGGAGA | 49 | 18 |
| AON 31 | UCCAGGAAAG | 44 | CUUUCCUGGA | 50 | 10 |

These AONs efficiently reduced exon 73 inclusion into the COL7A1 mRNA (see Table 1), while being devoid of any sequences that are less desirable from a manufacturability, purification and analytical perspective, or the chance of overall loss of function due to multiplexing.

The functionality of Collagen VII without the exon 73 can be addressed using several in vitro methods described in literature:

1. Protein analysis, both size and correct assembly of the α1-collagen chains, using western blotting (Titeux et al 2010). Of note, due to the small size of the skipped exon and the large size of the wild type protein, the apparent difference in protein size may not be picked-up.
2. Thermal stability analysis of the collagen VII homotrimer, by using western blotting under non-reduced conditions. Wild-type collagen VII is comprised of three α1-collagen a chains, and has a Tm of 41° C. (Mecklenbeck et al., 2002).
3. Cell migration analysis using colloidal gold or scratch assay. Compare the motility of fibroblasts and/or keratinocytes that express wild-type collagen VII vs the truncated protein without exon 73 (Chen et al. 2002).
4. Cell adhesion to various extracellular matrix components can be assessed, e.g. to collagen IV, laminin-332, laminin-1 or fibronectin (Chen et al. 2002).

The inventors postulate that the AONs shown to perform the best in terms of preventing, or at least reducing, exon 73 inclusion into the mammalian (preferably human) COL7A1 mRNA will provide satisfactory results in terms of collagen VII functionality, as can be readily assessed using the above methods from the prior art. Moreover, the AONs that comprise no more than two (preferably no more than one, such as one) CpG will perform satisfactorily in terms of in vivo immunogenicity. Hence, the most preferred AONs of the invention are candidates for development into therapeutics, suitable for therapy in humans suffering from, or at risk of suffering from, forms of dystrophic epidermolysis bullosa associated with mutations in exon 73 of the COL7A1 gene.

Example 2: Topical Delivery of Mh-AON1 Using an Ex Vivo Porcine Skin Model

Current wound management for DEB patients is mainly focused on wound care, management of itching and pain and early diagnosis of squamous cell carcinoma. Wound care includes cleaning and sterilizing of the wounds by the means of (chloride) baths, the use of chlorhexidine as a disinfectant and other antimicrobial creams. In addition the wounds are hydrated and moisturized using hydrogels to reduce pain and itch. Finally, wound care involves bandaging with different types of dressings/silicone foams to protect and reduce friction to the skin, prevent contamination, prevent sticking of material, absorb liquid from the wounds, to prevent blisters from growing in size, the blisters are punctured and drained to decrease the pressure from within.

Topical delivery of mh-AON1 provides a couple of advantages, firstly due to the local delivery there will be direct delivery to the target cells, keratinocytes and fibroblasts. Secondly due to the local administration systemic absorption will only be minor, resulting in less systemic toxicity (Wraight C J and White P J. Pharmacol Ther 2001 April; 90(1):89-104). Finally, it has been shown that after topical administration of oligonucleotides local concentrations in the dermis and epidermis can be up to 150 (for the dermis) and 4000 (for the epidermis) times as high as after systemic administration (Metha et al. J Invest Dermatol. 2000 November; 115(5):805-12).

To investigate the topical delivery of mh-AON1 an in-house ex vivo porcine skin model was established. Porcine skin is considered to be highly similar to human skin, with equal epidermal thickness and barrier properties of the stratum corneum. For the delivery studies, porcine ex vivo skin was received, cut to a thickness between 0.8 and 1.4 mm and cultured at the air-liquid interface with the apical site air exposed. In the wounds of DEB patients the epidermis is completely separated from the dermis, therefore these wounds were mimicked by mechanically removing the epidermis completely. To assess the skin penetration of mh-AON1 into intact or blister-like ex vivo porcine skin, the oligonucleotide was either formulated into PBS or into a hydrogel, part of DEB standard wound care. After exposure to mh-AON1 the skin pieces were fixed in 4% formalin, processed and embedded in paraffin for histological assessment using hematoxylin as a counterstaining for morphology. Since the oligonucleotide was conjugated to a Cy5 label the site of mh-AON1 could be visualized by fluorescent microscopy.

Mh-AON1 Formulated in PBS

Intact and blister-like ex vivo porcine skin pieces were incubated with 25 μg of mh-AON1 formulated into PBS for 24 hours after which they were processed for analysis. Results show that mh-AON1 added onto intact porcine skin pieces will not penetrate the stratum corneum (FIG. 4a-b). However, when the mh-AON1 formulation is incubated on the blister-like porcine skin, it was observed that the oligonucleotide had penetrated into the dermis (FIG. 4c-f).

Mh-AON1 Formulated into Hydrogels

For application onto patient wounds it is beneficial to incorporate mh-AON1 into an ointment or gel. Since DEB patients use hydrogels as part of their wound care, e.g. to moisturize the wounds and thereby decrease pain and itch, it was tested whether mh-AON1 could be incorporated into a hydrogel as well. For this purpose three different hydrogels were used: (1) Flaminal®, which is a hydrogel already used in patient care, (2) a hypromellose hydrogel and (3) a carbomer hydrogel both formulated in-house. All hydrogels are already commonly used in clinical settings. The hydrogel formulations were prepared with and without oligonucleotide, and spread on the skin pieces, 25 μg mh-AON1 was formulated into 50 mg of gel for each skin piece, giving an end concentration of 0.5 mg/ml oligonucleotide.

It was observed that mh-AON1 formulated into either Flaminal®, hypromellose or carbomer hydrogels could never penetrate the intact stratum corneum of the ex-vivo porcine skin pieces (FIG. 5*a, c, e, g*). However all three hydrogels could deliver the oligonucleotide into the dermis of the blister-like porcine skin where the epidermis was removed (FIG. 5*b, d, f, h*). Optimization the hydrogels is ongoing and selection of the final formulation will be based on the dermal penetration depth, local tolerability, pH of mh-AON1 combination, stability of the mh-AON1 hydrogel formulation and the release from mh-AON1 from the hydrogel.

Conclusion

DEB patients suffer greatly from their fragile skin due to blisters, wounds and ulcerations. Moreover they need constant wound care. mh-AON1 was therefore assessed via the topical route of delivery. Blister-like skin was created by removing the epidermis, including stratum corneum which mimics the DEB patient skin. It was demonstrated that mh-AON1 formulated in either PBS or a hydrogel is able to penetrate blister-like skin and reaches the dermis. These results support that topical administration to the patient's skin wounds is a feasible approach to deliver mh-AON1 to the target cells in the skin. Moreover, these findings support that a formulation resembling EB standard of care seems suitable in delivery of mh-AON1.

Example 3: Efficacy Testing at the mRNA Level

Two different cell types were used to assess the effectivity of mh-AON1: (1) HeLa and (2) skin derived human primary fibroblasts (HPF) from healthy individuals. Both cell types express COL7A1 mRNA and produce the collagen type VII protein. mh-AON1 as disclosed herein has been designed to exclude exon 73 from the COL7A1 mRNA, and thus exclude mutations from the transcript. Since mh-AON1 targets the splicing process, the most direct measurable outcome of efficacy is the profiling and quantification of COL7A1 transcripts (wild type and Δ73) with and without the addition of mh-AON1.

Profiling and Quantification of COL7A1 mRNA Level Through Polymerase Chain Reaction (PCR)

PCR is a straightforward technology which enables the logarithmic amplification of a specific DNA (cDNA) sequence. COL7A1 sequence-specific primers, flanking exon 73, were used to perform the PCR reaction. Afterwards the products formed were visualized using lab on a chips technology that allows discrimination of different fragment length products and the quantitative analysis based on yield.

For exon 73 skip experiments, HPF and HeLa cells were transfected with mh-AON1 at a concentration of 100 nM using polyethyleneimine (Poly I:C) as a transfection vehicle. 24 or 40 hours post transfection, the cells were harvested, whole mRNA isolated, cDNA synthesized and a PCR performed using COL7A1 specific primers, one in exon 69 and one in exon 74. As a negative control a scrambled (SCRM) version of the mh-AON1 oligonucleotide was taken along.

Results show that treatment with mh-AON1 leads to efficient exclusion of exon 73 from the COL7A1 mRNA compared to SCRM treated cells (FIG. 6) as determined by PCR. Furthermore, the level of wild type mRNA in untreated cells was comparable to the level of total COL7A1 mRNA in treated cells. Since the PCR/bioanalyzer method is informative but not absolute quantitative, these initial findings were followed up by using droplet digital PCR assays which offer highly accurate and absolute quantification of nucleic acid fragments.

Profiling and Quantification of COL7A1 mRNA Transcripts with Droplet Digital PCR Droplet digital PCR (ddPCR) provides a highly accurate and absolute quantification of nucleic acids through the partition of the PCR sample into thousands of droplets. The COL7A1 mRNA/cDNA PCR input was adjusted in such a way that each droplet contains either one or none COL7A1 cDNA molecule. To allow detection of the template, a probe specific for wild type or Δ73 COL7A1, was added to the PCR mix. The location of these probes are depicted in FIG. 7. One of the probes is specific for the wild type product, while the other probe is specific only for the Δ73 COL7A1 product. This probe upon binding to the template gets hydrolyzed and become fluorescent, so that after PCR amplification is performed, the fluorescent droplets containing the target sequence can be counted. Using Poisson statistical analysis of the numbers of positive and negative droplets, absolute quantitation of wild type or Δ73 COL7A1 mRNA molecules in the sample can be calculated.

HeLa cells were transfected with either 50, 100 or 200 nM mh-AON1 to establish a dose-response profile for mh-AON1. Results from 24 h after transfection show that treatment with mh-AON1 results in both COL7A1 wild type transcripts and Δ exon 73 transcripts. These results corroborate the observations seen with PCR. The dose of 50 nM already gives almost maximum effect after 24 h. After 40 h a small increase in the % of Δ exon 73 transcripts was observed for the 50 nM and 200 nM transfection (FIG. 8).

Example 4: In Vitro Immunogenicity Tests

Oligonucleotides have the potential to cause activation of pattern recognition receptors (PRR) of the vertebrate innate immune system. The best studied family of PRR receptors are the toll-like receptors (TLRs). TLRs are a class of proteins that play a key role in the innate immune system. They are single, membrane-spanning, non-catalytic receptors that are usually expressed in macrophages and dendritic cells that recognize structurally-conserved molecules derived from microbes. TLRs that are activated by different types of nucleic acids are those located on endosomes: TLR 3 (recognizes double stranded RNA); TLR7/8 (recognizes double and single stranded RNA); and TLR9 (recognizes CpG-DNA).

Upon recognition of these components by the PRRs, a specific 'antimicrobial' immune response is triggered. TLR activation results in the activation of nuclear factor kappa-light-chain-enhancer of activated B cells (NE-κB), Interferon regulatory factor 3 (IRF-3) and activator protein 1 (AP-1). Activation of AP-1, IRF-3 and NE-κB results in the production of inflammatory cytokines, type-I interferons and other mediators of the innate immune response. These processes not only trigger immediate host defensive responses such as inflammation, but also prime and orchestrate antigen-specific adaptive immune responses.

In vitro exposure of primary human peripheral blood mononuclear cells (PBMC) to mh-AON1 was used to assess (systemic) drug-specific immune responses and immunotoxicity. The in vitro assay using PBMC is an established preclinical test using the production of (inflammatory) cytokines as surrogate marker for systemic immune responses. The PBMC assay enables prediction of tolerability as a factor of the immunogenicity and allergenicity potential of investigational compounds, and could enable an estimation of a safe dosing range for these compounds.

For the studies of mh-AON1, in-house isolated PBMC were used, acquired from buffy coats of healthy blood bank donors. Production of the key pro-inflammatory cytokines in the culture supernatant was assessed after 24 h of stimulation with mh-AON1 at concentrations ranging from 10 nM to 1 µM. In addition, the Ramos-Blue (Invivogen, human B cells) reporter cell line with chromosomal integration of a secreted embryonic alkaline phosphatase reporter construct inducible by NE-κB and/or AP-1 was used to assess general PPR-mediated immune activation by mh-AON1 and AON73.24.5. Ramos-Blue cells express the relevant set of TLRs, including: TLR3, −7/8 and −9. Activation NE-κB and/or AP-1 was measured after 24 h of stimulation with mh-AON1 or AON73.25.4 at concentrations ranging from 10 nM to 1 µM. Moreover, the viability of the PBMC and Ramos-Blue after treatment with mh-AON1 was analyzed by measuring the fluorescent resorufin in the culture supernatant to assess potential cytoxic effect of mh-AON1. Viable cells convert the non-fluorescent resazurin into fluorescent resorufin.

Results in Human PBMC

Stimulation of human PBMC with the positive controls LPS (TLR4 agonist) and R848 (TLR7/8 agonist) resulted in significantly increased concentrations of all measured cytokines, except IL-3, in the culture supernatant. Moreover, stimulation with CpG DNA (TLR9 agonist) or Poly (I:C) (TLR3 agonist) induced a similar pattern of cytokines, although to a lesser extent. A Heat map depicting the significance levels of cytokine concentrations in culture supernatant after stimulation with mh-AON1 or the positive controls compared to saline-treated human PBMC is shown in FIG. 9a. Importantly, stimulation of human PBMC with mh-AON1 concentrations ranging from 10 nM to 1 µM did not results in increased concentrations of any of the measured cytokines in the culture supernatant, with the exception of IFN-α2 at the lowest concentration mh-AON1 (FIG. 9a). However, since the increase in concentration of IFN-α2 in the supernatant after stimulation with mh-AON1 is not dose dependent, this was considered as an experimental outlier or technical error (FIG. 9b). Finally, there were no signs of cytotoxicity 24 h after treatment with mh-AON1 (FIG. 9c). In contrast, there was a slight increase in viability observed after treatment with R848, or 10 nM and 100 nM mh-AON1 suggesting enhanced cell survival, increased cell metabolism or even increased proliferation/differentiation.

Results in Ramos-Blue Cells

Results of the immunogenicity assay carried out in the human Ramos Blue cell line showed no activation of NE-κB and/or AP-1 after 24 h treatment with mh-AON1 or AON73.24.5 at concentrations ranging from 10 nM to 1 µM (FIG. 10a). In contrast, the positive controls Poly(I:C) (1 µg/ml), CpG (10 µg/ml) and R848 (1 µM) did induce activation of NE-κB and/or AP-1. LPS had no effect, since TLR4 is not expressed on Ramos-Blue. Moreover, there were no signs of cytotoxicity 24 h after treatment with MH-AON1 (FIG. 10b) confirming the results obtained in human PBMC.

It will be understood that the invention is described above by way of example only and modifications may be made whilst remaining within the scope and spirit of the invention.

The invention claimed is:

1. An antisense oligoribonucleotide capable of preventing or reducing exon 73 inclusion into a human collagen type VII alpha 1 chain (COL7A1) mRNA when the mRNA is produced by splicing from a pre-mRNA in a human cell, wherein the oligoribonucleotide comprises a nucleotide sequence having a length of between 12 and 24 nucleotides that is at least 95% complementary to a target nucleotide sequence in a COL7A1 pre-mRNA, wherein the target nucleotide sequence is fully complementary to SEQ ID NO: 5, 24, 25, 26, 27, 28, 39, 40, 41, 42, 43, 29, or 35, and wherein the oligoribonucleotide comprises at least one nucleotide analogue or equivalent.

2. The antisense oligoribonucleotide of claim 1, wherein the oligoribonucleotide can anneal to the target nucleotide sequence in a COL7A1 pre-RNA molecule under physiological conditions, thereby facilitating skipping of exon 73.

3. The antisense oligoribonucleotide of claim 1, wherein the target nucleotide sequence is fully complementary to SEQ ID NO: 35.

4. The antisense oligoribonucleotide of claim 1, wherein
(a) the oligoribonucleotide has no more than two CpG sequences;
(b) the oligoribonucleotide has a non-natural internucleoside linkage; and/or
(c) the nucleotide analogue or equivalent comprises (i) a modified ribose moiety comprising a lower 2'-O-alkyl modification, a 2'-O-alkyl-O-alkyl modification, or a 2'-methoxyethoxy modification; or (ii) a locked nucleic acid (LNA), in which the 2'-carbon atom is linked to the 3' or 4' carbon atom of the ribose ring, thereby forming a bicyclic ribose moiety.

5. The antisense oligoribonucleotide of claim 4, wherein
(a) the oligoribonucleotide has no more than one CpG sequence;
(b) the oligoribonucleotide has a length of between 16 and 23 nucleotides;
(c) the oligoribonucleotide has a phosphorothioate internucleoside linkage; and/or
(d) the nucleotide analogue or equivalent comprises (i) a modified ribose moiety comprising a 2'-O-methyl modification; or (ii) an LNA, in which the 2'-carbon atom is linked to the 4' carbon atom of the ribose ring by a 2'-O, 4'-C-ethylene bridge.

6. The antisense oligoribonucleotide of claim 5, wherein
(a) all the internucleoside linkages of the oligoribonucleotide are phosphorothioate linkages; and/or
(b) all the nucleotides of the oligoribonucleotide are nucleotide analogues or equivalents comprising (i) a modified ribose moiety comprising a 2'-O-methyl modification; or (ii) an LNA, in which the 2'-carbon atom is linked to the 3' or 4' carbon atom of the ribose ring.

7. The antisense oligoribonucleotide of claim 1, wherein the oligoribonucleotide is capable of reducing exon 73 inclusion in a HeLa cell, or a sample derived therefrom, by more than 70%.

8. The antisense oligoribonucleotide of claim 7, wherein the oligoribonucleotide is capable of reducing exon 73 inclusion in a HeLa cell, or a sample derived therefrom, by more than 80%.

9. The antisense oligoribonucleotide of claim 8, wherein the oligoribonucleotide is capable of reducing exon 73 inclusion in a HeLa cell, or a sample derived therefrom, by more than 90%.

10. A composition comprising the antisense oligoribonucleotide of claim 1 and one or more of a carrier, excipient, stabilizer, transfection agent, diluent, gelling agent, and buffer.

11. The composition of claim 10, which is a pharmaceutical composition for use in a human suffering from, or at risk of suffering from, forms of dystrophic epidermolysis bullosa associated with mutations in exon 73 of the COL7A1 gene.

12. A method for preventing or reducing exon 73 inclusion into a human COL7A1 mRNA when said mRNA is produced by splicing from an RNA transcript in a human cell, the method comprising providing to the cell the antisense oligoribonucleotide of claim 1, under conditions conducive to uptake of the oligoribonucleotide by the cell, and allowing splicing to take place.

13. The method of claim 12, wherein the antisense oligoribonucleotide comprises the nucleotide sequence of SEQ ID NO: 35.

14. The method of claim 12, wherein the antisense oligoribonucleotide consists of the nucleotide sequence of SEQ ID NO: 35.

15. The method of claim 14, wherein
(a) the oligoribonucleotide has a phosphorothioate internucleoside linkage; and/or
(b) the nucleotide analogue or equivalent comprises (i) a modified ribose moiety comprising a 2'-O-methyl modification; or (ii) an LNA, in which the 2'-carbon atom is linked to the 3' or 4' carbon atom of the ribose ring.

* * * * *